US012653629B2

(12) United States Patent
Sharon et al.

(10) Patent No.: US 12,653,629 B2
(45) Date of Patent: Jun. 16, 2026

(54) COMPACT ROBOTIC DEVICE AND ASSEMBLIES FOR MANIPULATION OF ELONGATE SURGICAL TOOLS

(71) Applicants:Microbot Medical Ltd., Yokneam Illit (IL); Technion Research & Development Foundation Limited, Haifa (IL)

(72) Inventors: Simon Sharon, Zichron Yaacov (IL); Idan Boader, Karmiel (IL); Evgeny Kofman, Kiriat-Motzkin (IL); Zev Sohn, Karnei Shomron (IL); Moshe Shoham, Haifa (IL); Eran Cohen, Kiryat-Tivon (IL); Eyal Morag, Tel Aviv (IL)

(73) Assignees: Microbot Medical Ltd., Yokneam Illit (IL); Technion Research & Development Foundation Limited, Haifa (IL)

( * ) Notice: Subject to any disclaimer, the term of this patent is extended or adjusted under 35 U.S.C. 154(b) by 329 days.

(21) Appl. No.: 18/287,470

(22) PCT Filed: Mar. 17, 2022

(86) PCT No.: PCT/IL2022/050303
§ 371 (c)(1),
(2) Date: Oct. 19, 2023

(87) PCT Pub. No.: WO2022/224234
PCT Pub. Date: Oct. 27, 2022

(65) Prior Publication Data
US 2024/0197415 A1 Jun. 20, 2024

Related U.S. Application Data

(63) Continuation-in-part of application No. 17/233,774, filed on Apr. 19, 2021, now Pat. No. 11,291,515.
(Continued)

(51) Int. Cl.
*A61B 34/30* (2016.01)
*A61M 25/00* (2006.01)

(52) U.S. Cl.
CPC ........ *A61B 34/30* (2016.02); *A61B 2034/301* (2016.02); *A61M 25/0082* (2013.01)

(58) Field of Classification Search
CPC ..... A61B 1/00147; A61B 34/30; A61B 34/35; A61B 34/37; A61B 34/70;
(Continued)

(56) References Cited

U.S. PATENT DOCUMENTS

| | | | |
|---|---|---|---|
| 3,789,841 A | 2/1974 | Antoshkiw | |
| 5,571,072 A | 11/1996 | Kronner | |

(Continued)

FOREIGN PATENT DOCUMENTS

| | | |
|---|---|---|
| CA | 2918879 | 1/2015 |
| CN | 101918073 | 12/2010 |

(Continued)

OTHER PUBLICATIONS

International Preliminary Report on Patentability Dated Feb. 8, 2024 From the International Bureau of WIPO Re. Application No. PCT/IL2022/050756 (10 Pages).
(Continued)

*Primary Examiner* — Nathaniel C Chukwurah

(57) ABSTRACT

An assembly for driving movement of an elongate surgical tool, comprising:
a plurality of adjacent pairs of driving wheels, each pair of driving wheels having a space therebetween such that spaces
(Continued)

of the plurality of pairs of driving wheels are axially aligned to form a channel for the elongate surgical tool to extend through;

wherein at least one pair of driving wheels out of the plurality of pairs is arranged to lie on a plane different than a plane on which at least one other pair of driving wheels lies.

15 Claims, 17 Drawing Sheets

Related U.S. Application Data

(60) Provisional application No. 63/195,020, filed on May 30, 2021.

(58) Field of Classification Search
    CPC .... A61B 2017/00477; A61B 2034/301; A61B 2090/062; A61M 25/0113; A61M 25/09041; A61M 2025/0042; B25J 9/0021; B25J 9/102
    See application file for complete search history.

(56) References Cited

U.S. PATENT DOCUMENTS

| | | | |
|---|---|---|---|
| 6,017,354 | A | 1/2000 | Culp et al. |
| 6,171,234 | B1 | 1/2001 | White et al. |
| 6,290,675 | B1 | 9/2001 | Vujanic et al. |
| 6,358,199 | B1 | 3/2002 | Pauker et al. |
| 6,726,675 | B1 | 4/2004 | Beyar |
| 7,615,042 | B2 | 11/2009 | Beyar et al. |
| 8,317,745 | B2 | 11/2012 | Kirschenman et al. |
| 8,423,182 | B2 | 4/2013 | Robinson et al. |
| 8,480,618 | B2 * | 7/2013 | Wenderow ....... A61B 17/00234 604/95.01 |
| 8,894,610 | B2 | 11/2014 | Macnamara et al. |
| 9,192,745 | B2 | 11/2015 | Bencteux et al. |
| 9,795,764 | B2 | 10/2017 | Pacheco et al. |
| 10,149,680 | B2 | 12/2018 | Parihar et al. |
| 10,376,323 | B2 | 8/2019 | Farritor et al. |
| 10,524,867 | B2 | 1/2020 | Kokish et al. |
| 10,543,047 | B2 * | 1/2020 | Yu .......................... A61B 34/30 |
| 10,820,952 | B2 | 11/2020 | Yu |
| 10,980,608 | B2 | 4/2021 | Scheib et al. |
| 2002/0133077 | A1 | 9/2002 | Edwardsen et al. |
| 2002/0177789 | A1 | 11/2002 | Ferry et al. |
| 2004/0254566 | A1 | 12/2004 | Picchi et al. |
| 2005/0021065 | A1 | 1/2005 | Yamada et al. |
| 2005/0197566 | A1 | 9/2005 | Strommer et al. |
| 2008/0097465 | A1 | 4/2008 | Rollins et al. |
| 2009/0247944 | A1 | 10/2009 | Kirschenman et al. |
| 2011/0028894 | A1 | 2/2011 | Foley et al. |
| 2011/0105954 | A1 | 5/2011 | Cohen et al. |
| 2011/0130718 | A1 | 6/2011 | Kidd |
| 2012/0110824 | A1 | 5/2012 | Smith et al. |
| 2013/0123803 | A1 | 5/2013 | Kirschenman |
| 2014/0243742 | A1 | 8/2014 | Pacheco et al. |
| 2014/0276647 | A1 | 9/2014 | Yu |
| 2014/0276935 | A1 | 9/2014 | Yu |
| 2014/0277333 | A1 | 9/2014 | Lewis et al. |
| 2014/0305993 | A1 | 10/2014 | Timm et al. |
| 2014/0309659 | A1 | 10/2014 | Roh et al. |
| 2015/0001968 | A1 | 1/2015 | Zirps |
| 2015/0094732 | A1 | 4/2015 | Pacheco et al. |
| 2015/0112362 | A1 | 4/2015 | Inoue et al. |
| 2015/0374956 | A1 | 12/2015 | Bogusky |
| 2016/0030709 | A1 | 2/2016 | Losordo |
| 2016/0157941 | A1 | 6/2016 | Anvari et al. |
| 2016/0361128 | A1 | 12/2016 | Seeber |
| 2017/0105804 | A1 | 4/2017 | Yu |
| 2018/0055588 | A1 | 3/2018 | Yanagihara et al. |
| 2018/0228557 | A1 | 8/2018 | Darisse et al. |
| 2019/0125397 | A1 | 5/2019 | Arnold et al. |
| 2019/0201120 | A1 | 7/2019 | Shelton, IV et al. |
| 2019/0223967 | A1 | 7/2019 | Abbott et al. |
| 2019/0328599 | A1 | 10/2019 | Mahoney |
| 2020/0146759 | A1 | 5/2020 | Schena et al. |
| 2020/0155245 | A1 | 5/2020 | Yu |
| 2020/0163726 | A1 | 5/2020 | Tanner et al. |
| 2020/0222668 | A1 | 7/2020 | Wenderow et al. |
| 2020/0281666 | A1 | 9/2020 | Gunn et al. |
| 2021/0052339 | A1 | 2/2021 | Choi et al. |
| 2021/0236217 | A1 | 8/2021 | Sharon et al. |
| 2021/0251709 | A1 | 8/2021 | Sharon et al. |
| 2021/0282875 | A1 | 9/2021 | Sharon et al. |
| 2022/0071723 | A1 | 3/2022 | Sharon et al. |
| 2023/0009618 | A1 | 1/2023 | Sharon et al. |
| 2023/0346495 | A1 | 11/2023 | Sharon et al. |
| 2024/0358448 | A1 | 10/2024 | Boader et al. |

FOREIGN PATENT DOCUMENTS

| | | |
|---|---|---|
| CN | 103442660 | 12/2013 |
| CN | 103599585 | 2/2014 |
| CN | 111529065 | 8/2020 |
| DE | 102004007935 | 5/2005 |
| EP | 1061990 | 9/2004 |
| EP | 2347785 | 7/2011 |
| IL | 123646 | 5/2010 |
| IT | 201800009380 | 4/2020 |
| JP | 10-212067 | 8/1998 |
| JP | 2002-525182 | 8/2002 |
| JP | 2010-253168 | 11/2010 |
| JP | 2011-509763 | 3/2011 |
| JP | 2011-519678 | 7/2011 |
| JP | 2015-523148 | 8/2015 |
| JP | 2017-104581 | 6/2017 |
| KR | 10-2129337 | 7/2020 |
| WO | WO 99/45994 | 9/1999 |
| WO | WO 2018/071505 | 4/2018 |
| WO | WO 2019/070696 | 4/2019 |
| WO | WO 2019/173107 | 9/2019 |
| WO | WO 2019/195841 | 10/2019 |
| WO | WO 2019/203616 | 10/2019 |
| WO | WO 2020/072543 | 4/2020 |
| WO | WO 2021/011551 | 1/2021 |
| WO | WO 2021/011554 | 1/2021 |
| WO | WO 2021/065311 | 4/2021 |
| WO | WO 2021/105997 | 6/2021 |
| WO | WO 2021/105998 | 6/2021 |
| WO | WO 2021/105999 | 6/2021 |
| WO | WO 2022/224234 | 10/2022 |
| WO | WO 2023/007478 | 2/2023 |

OTHER PUBLICATIONS

Requisition by the Examiner Dated Jan. 4, 2024 From the Innovation, Science and Economic Development Canada, Canadian Intellectual Property Office Re. Application No. 3,156,099. (16 Pages).

Requisition by the Examiner Dated Aug. 15, 2024 From the Innovation, Science and Economic Development Canada, Canadian Intellectual Property Office Re. Application No. 3,159,753. (11 Pages).

Official Action Dated Mar. 14, 2024 from the US Patent and Trademark Office Re. U.S. Appl. No. 17/526,060. (30 pages).

Notice of Reasons for Rejection Dated Sep. 3, 2024 From the Japan Patent Office Re. Application No. 2022-530811. and its Translation Into English. (20 Pages).

English Summary Dated May 27, 2024 of Notification of Office Action and Search Report Dated May 10, 2024 From the National Intellectual Property Administration of the People's Republic of China Re. Application No. 202080092059.1. (2 Pages).

Notice of Allowance Dated May 30, 2024 from the US Patent and Trademark Office Re. U.S. Appl. No. 17/526,060. (5 pages).

Office Action Dated May 26, 2024 From the Israel Patent Office Re. Application No. 298418. (5 Pages).

Restriction Official Action Dated May 30, 2024 from the US Patent and Trademark Office Re. U.S. Appl. No. 17/780,039. (6 pages).

(56) References Cited

OTHER PUBLICATIONS

Requisition by the Examiner Dated Dec. 19, 2023 From the Innovation, Science and Economic Development Canada, Canadian Intellectual Property Office Re. Applicaiton No. 3,159,753. (13 Pages).
Requisition by the Examiner Dated Apr. 25, 2024 From the Innovation, Science and Economic Development Canada, Canadian Intellectual Property Office Re. Application No. 3,161,955 with claims. (10 Pages).
Restriction Official Action Dated Apr. 25, 2024 from the US Patent and Trademark Office Re. U.S. Appl. No. 17/780,039. (10 pages).
Notice of Reason(s) for Rejection Dated Nov. 11, 2025 From the Japan Patent Office Re. Application No. 2023-564058 and Its Translation Into English. (15 Pages).
Notice of Reason(s) for Rejection Dated Jul. 23, 2024 From the Japan Patent Office Re. Application No. 2022-528230 and Its Translation Into English. (20 Pages).
Machine Translation Dated Jul. 24, 2024 of Notification of Office Action and Search Report Dated Jul. 16, 2024 From the State Intellectual Property Office of the People's Republic of China Re. Application No. 202080086796.0. (7 Pages).
Notice of Reason(s) for Rejection Dated Jul. 16, 2024 From the Japan Patent Office Re. Application No. 2022-530812 and Its Translation Into English. (29 Pages).
Notification of Office Action and Search Report Dated Jul. 16, 2024 From the State Intellectual Property Office of the People's Republic of China Re. Application No. 202080086796.0. (8 Pages).
European Search Report and the European Search Opinion Dated Sep. 1, 2022 From the European Patent Office Re. Application No. 22168338.6. (9 Pages).
International Preliminary Report on Patentability Dated Nov. 2, 2023 From the International Bureau of WIPO Re. Application No. PCT/IL2022/050303 (10 Pages).
International Preliminary Report on Patentability Dated Jun. 9, 2022 From the International Bureau of WIPO Re. Application No. PCT/IL2020/051224. (10 Pages).
International Preliminary Report on Patentability Dated Jun. 9, 2022 From the International Bureau of WIPO Re. Application No. PCT/IL2020/051225. (7 Pages).
International Preliminary Report on Patentability Dated Jun. 9, 2022 From the International Bureau of WIPO Re. Application No. PCT/IL2020/051226. (11 Pages).
International Search Report and the Written Opinion Dated Dec. 1, 2022 From the International Searching Authority Re. Application No. PCT/IL2022/050756. (15 Pages).
International Search Report and the Written Opinion Dated Jul. 5, 2022 From the International Searching Authority Re. Application No. PCT/IL2022/050303. (19 Pages).
International Search Report and the Written Opinion Dated Feb. 15, 2021 From the International Searching Authority Re. Application No. PCT/IL2020/051224. (24 Pages).
International Search Report and the Written Opinion Dated Feb. 18, 2021 From the International Searching Authority Re. Application No. PCT/IL2020/051226. (18 Pages).
International Search Report and the Written Opinion Dated Feb. 25, 2021 From the International Searching Authority Re. Application No. PCT/IL2020/051225. (14 Pages).
Interview Summary Dated Nov. 19, 2021 from US Patent and Trademark Office Re. U.S. Appl. No. 17/233,774. (3 pages).
Interview Summary Dated Oct. 20, 2021 from US Patent and Trademark Office Re. U.S. Appl. No. 17/331,837. (2 pages).
Invitation to Pay Additional Fees and Communication Relating to the Results of the Partial International Search Dated Jan. 12, 2021 From the International Searching Authority Re. Application No. PCT/IL2020/051224. (13 Pages).
Invitation to Pay Additional Fees and Communication Relating to the Results of the Partial International Search Dated Oct. 27, 2022 From the International Searching Authority Re. Application No. PCT/IL2022/050756. (5 Pages).

Notice of Allowance Dated Nov. 12, 2021 together with Interview Summary from the US Patent and Trademark Office Re. U.S. Appl. No. 17/331,837. (11 pages.
Notice of Allowance Dated Aug. 20, 2021 from the US Patent and Trademark Office Re. U.S. Appl. No. 17/187,936. (7 pages).
Notice of Allowance Dated Dec. 22, 2021 from US Patent and Trademark Office Re. U.S. Appl. No. 17/233,774. (12 pages).
Office Action and Search Report Dated Jun. 4, 2023 From the Israel Patent Office Re. Application No. 298418. (10 Pages).
Office Action Dated Aug. 30, 2023 From the Israel Patent Office Re. Application No. 300398. (5 Pages).
Official Action & Interview Summary Dated Sep. 2, 2021 From the US Patent and Trademark Office Re. U.S. Appl. No. 17/233,774. (23 Pages).
Official Action Dated Aug. 2, 2021 from the US Patent and Trademark Office Re. U.S. Appl. No. 17/331,837. (19 pages).
Official Action Dated Jun. 23, 2021 From the US Patent and Trademark Office Re. U.S. Appl. No. 17/187,936. (13 Pages).
Official Action Dated Nov. 24, 2023 from the US Patent and Trademark Office Re. U.S. Appl. No. 17/526,060. (41 pages).
Requisition by the Examiner Dated Oct. 25, 2023 From the Innovation, Science and Economic Development Canada, Canadian Intellectual Property Office Re. Application No. 3,161,955 with claims. (14 Pages).
Restriction Official Action Dated Jul. 16, 2021 from the US Patent and Trademark Office Re. U.S. Appl. No. 17/233,774. (5 pages).
Supplementary European Search Report and the European Search Opinion Dated Nov. 7, 2023 From the European Patent Office Re. Application No. 20893145.1. (8 Pages).
Notification of Office Action and Search Report Dated May 10, 2024 From the National Intellectual Property Administration of the People's Republic of China Re. Application No. 202080092059.1 and Its Machine Translation Into English. (18 Pages).
Notification of Office Action and Search Report Dated Oct. 8, 2024 From the State Intellectual Property Office of the People's Republic of China Re. Application No. 202080094557.X and its Machine Translation. (15 Pages).
Official Action Dated Oct. 23, 2024 From the US Patent and Trademark Office Re. U.S. Appl. No. 17/780,039. (71 Pages).
Notification of Office Action and Search Report Dated Nov. 7, 2024 From the National Intellectual Property Administration of the People's Republic of China Re. Application No. 202080092059.1 and ItsSummary Translation Into English. (4 Pages).
Office Action Dated Jan. 11, 2024 From the Israel Patent Office Re. Application No. 297409. (6 Pages).
Office Action Dated Jan. 11, 2024 From the Israel Patent Office Re. Application No. 300398. (4 Pages).
Supplementary European Search Report and the European Search Opinion Dated Mar. 3, 2025 From the European Patent Office Re. Application No. 22791251.6. (11 Pages).
Supplementary European Search Report and the European Search Opinion Dated Jan. 12, 2024 From the European Patent Office Re. Application No. 20892205.4. (8 Pages).
Requisition by the Examiner Dated Jan. 17, 2024 From the Innovation, Science and Economic Development Canada, Canadian Intellectual Property Office Re. Application No. 3,161,864. (12 Pages).
Summary Dated Oct. 30, 2024 of Notification of Office Action Dated Oct. 8, 2024 From the State Intellectual Property Office of the People's Republic of China Re. Application No. 202080094557.X. (4 Pages).
Supplementary European Search Report and the European Search Opinion Dated Dec. 5, 2023 From the European Patent Office Re. Application No. 20891520.7. (11 Pages).
English Summary Dated Aug. 5, 2024 of Notification of Office Action Dated Jul. 16, 2024 From the State Intellectual Property Office of the People's Republic of China Re. Application No. 202080086796.0. (2 Pages).
Office Action Dated Feb. 25, 2026 From the Israel Patent Office Re. Application No. 307833. (4 Pages).

* cited by examiner

FIG. 2A
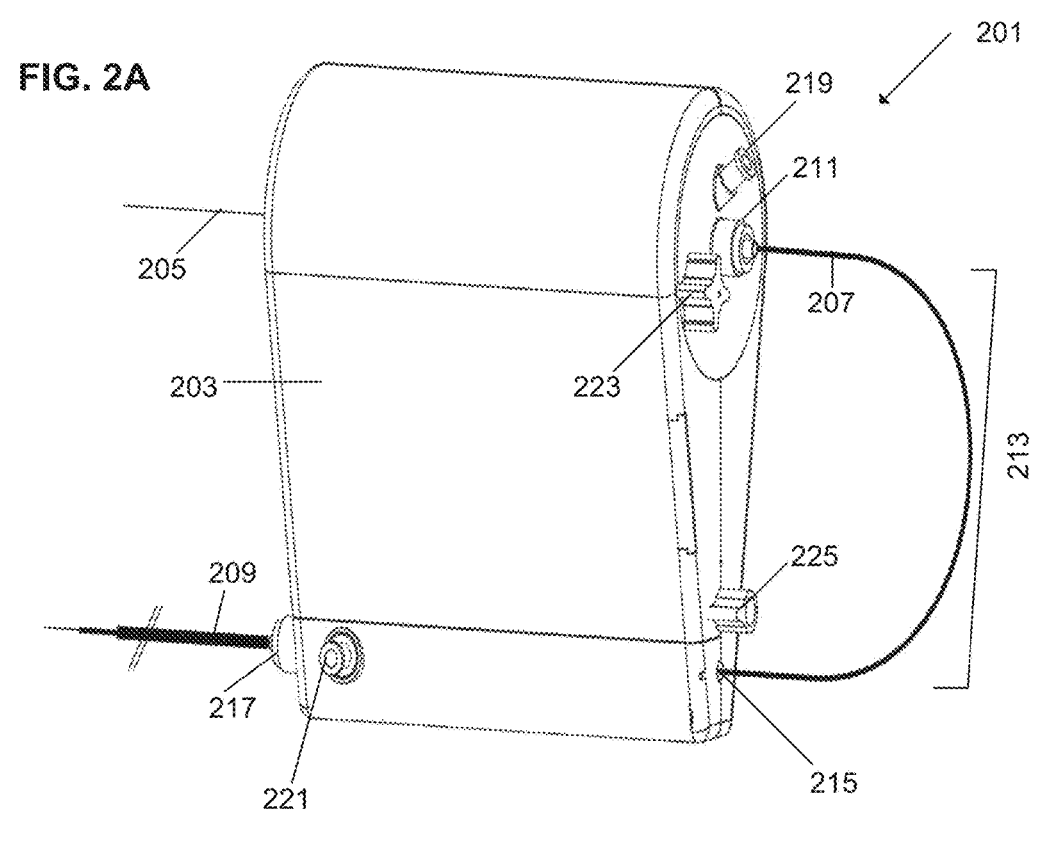
FIG. 2B                                        FIG. 2C
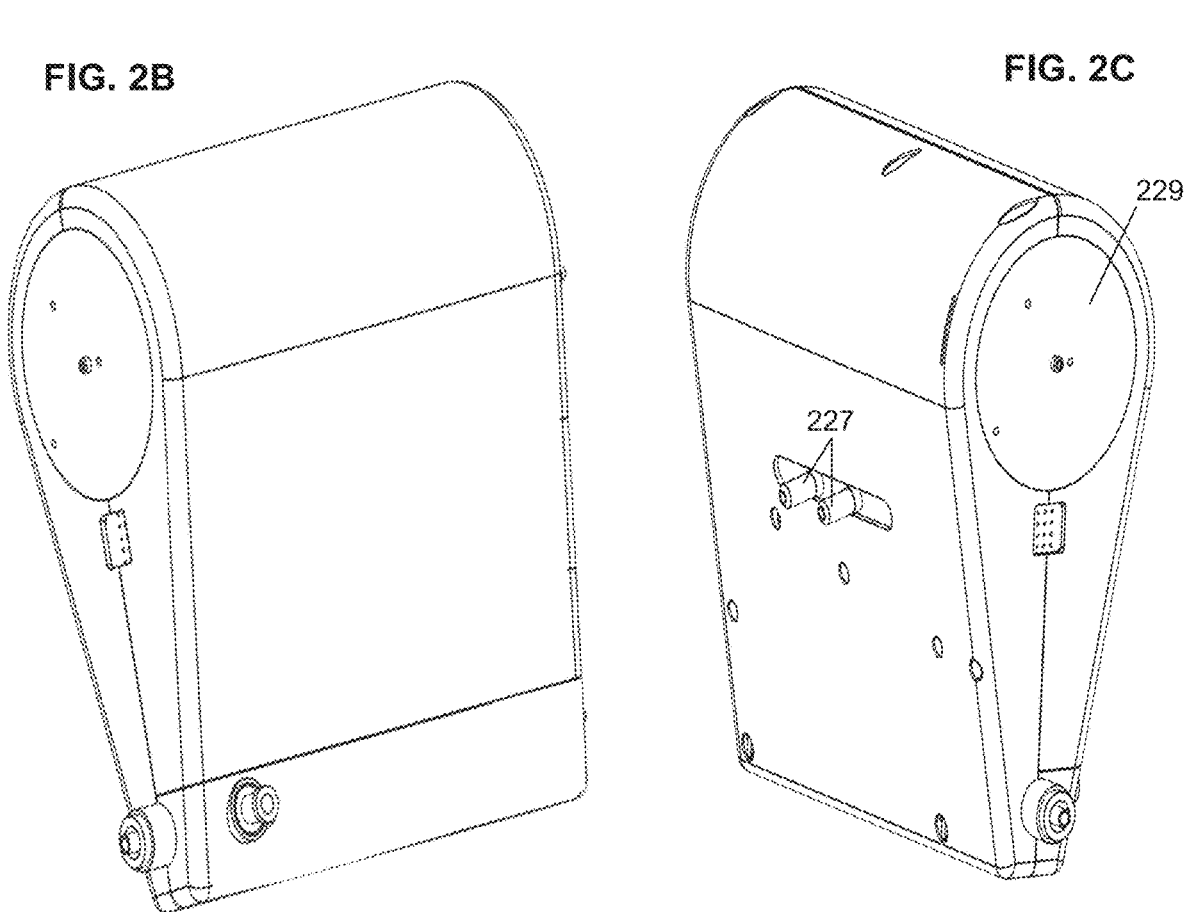

FIG. 11A

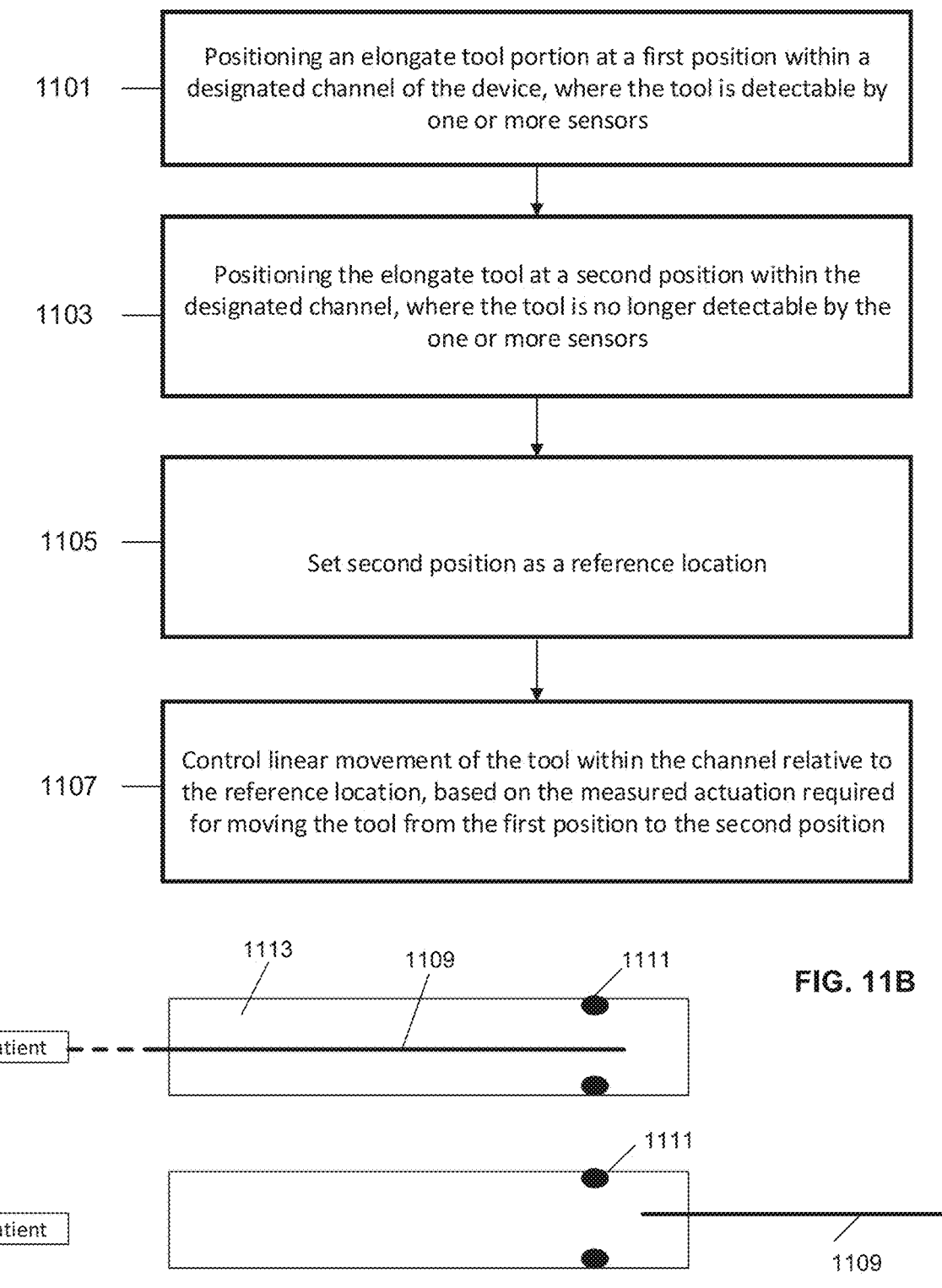

1101 — Positioning an elongate tool portion at a first position within a designated channel of the device, where the tool is detectable by one or more sensors 1103 — Positioning the elongate tool at a second position within the designated channel, where the tool is no longer detectable by the one or more sensors 1105 — Set second position as a reference location 1107 — Control linear movement of the tool within the channel relative to the reference location, based on the measured actuation required for moving the tool from the first position to the second position 1113    1109    1111 patient

FIG. 11B

1111 patient

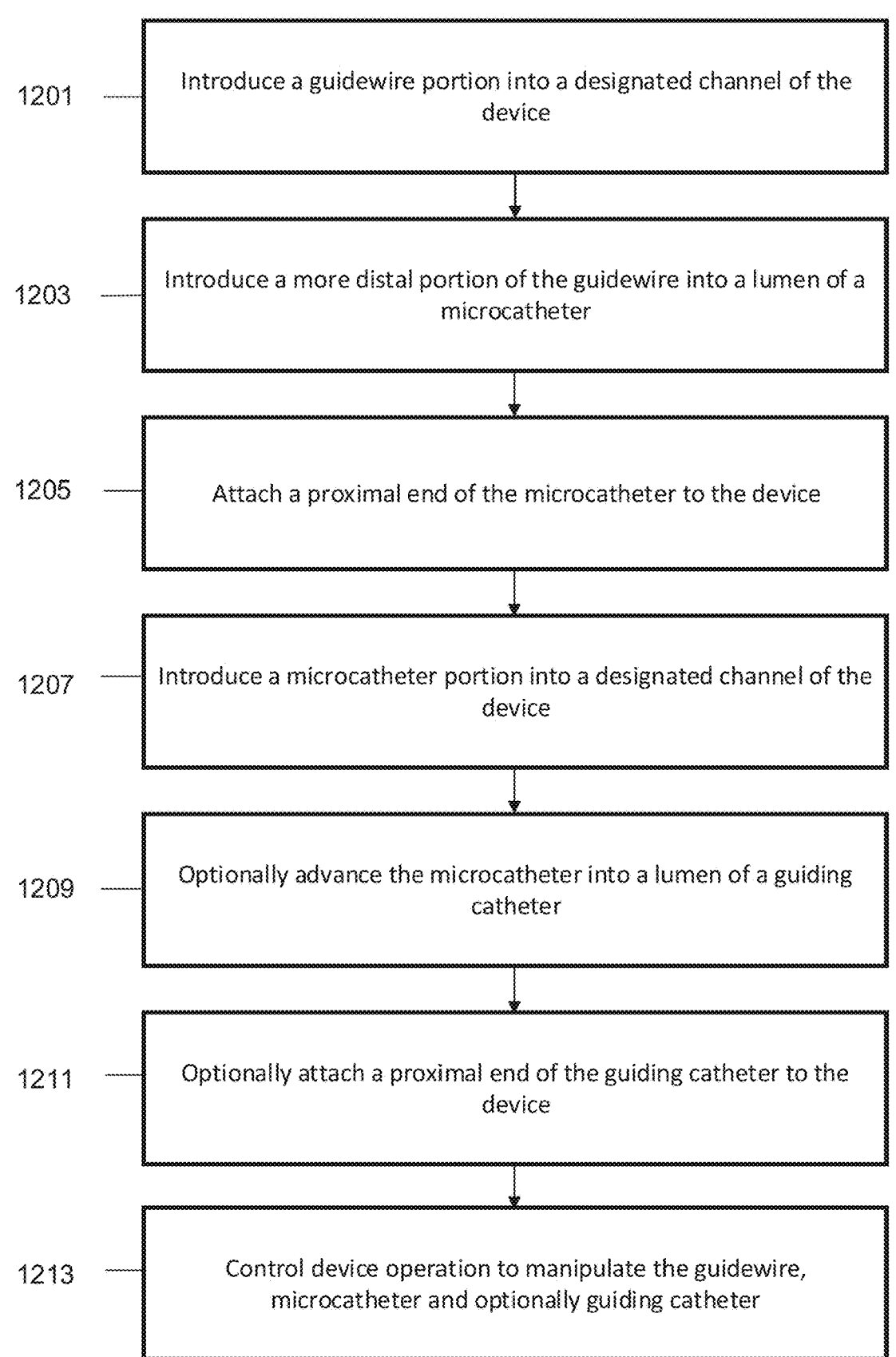

1201 —— Introduce a guidewire portion into a designated channel of the device

1203 —— Introduce a more distal portion of the guidewire into a lumen of a microcatheter 1205 —— Attach a proximal end of the microcatheter to the device 1207 —— Introduce a microcatheter portion into a designated channel of the device 1209 —— Optionally advance the microcatheter into a lumen of a guiding catheter 1211 —— Optionally attach a proximal end of the guiding catheter to the device 1213 —— Control device operation to manipulate the guidewire, microcatheter and optionally guiding catheter

FIG. 12

COMPACT ROBOTIC DEVICE AND ASSEMBLIES FOR MANIPULATION OF ELONGATE SURGICAL TOOLS

RELATED APPLICATIONS

This application is a National Phase of PCT Patent Application No. PCT/IL2022/050303 having International filing date of Mar. 17, 2022, which is a Continuation-in-Part (CIP) of U.S. patent application Ser. No. 17/233,774 filed on Apr. 19, 2021, now U.S. Pat. No. 11,291,515.

PCT Patent Application No. PCT/IL2022/050303 also claims the benefit of priority of U.S. Provisional Patent Application No. 63/195,020 filed on May 30, 2021.

The contents of the above applications are all incorporated by reference as if fully set forth herein in their entirety.

FIELD AND BACKGROUND OF THE INVENTION

The present invention, in some embodiments thereof, relates to devices and assemblies for robotic manipulation of elongate surgical tools and, more particularly, but not exclusively, to compactly arranged and packed mechanisms for linearly moving and/or rolling an elongate surgical tool.

U.S. Pat. No. 8,480,618 to Wenderow et al. discloses: "A robotic catheter system is provided. The robotic catheter system includes a housing and a drive assembly coupled to the housing. The drive assembly is configured to impart movement to a catheter device. The catheter system includes a release structure permitting the drive assembly to be decoupled and removed from the housing without removing the catheter device from a patient."

SUMMARY OF THE INVENTION

According to an aspect of some embodiments there is provided an assembly for driving movement of an elongate surgical tool, comprising:

a plurality of adjacent pairs of driving wheels, each pair of driving wheels having a space therebetween such that spaces of the plurality of pairs of driving wheels are axially aligned to form a channel for the elongate surgical tool to extend through;

wherein at least one pair of driving wheels out of the plurality of pairs is arranged to lie on a plane different than a plane on which at least one other pair of driving wheels lies.

In some embodiments, the plurality of pairs of driving wheels are arranged to lie on a first plane and on a second plane, the second plane crossing the first plane.

In some embodiments, the plurality of pairs of driving wheels are interveningly disposed on the first and second planes.

In some embodiments, the second plane is perpendicular to the first plane.

In some embodiments, at least one driving wheel of each of the pairs is moveable between a first position in which the driving wheel is distanced from its opposing driving wheel, and a second position in which the driving wheel is within a distance from its opposing driving wheel which is equal to or shorter than a diameter of an elongate surgical tool received between the wheels.

In some embodiments, the assembly comprises a single knob configured to move wheels of all of the wheel pairs between the first position and the second position.

In some embodiments, the assembly comprises at least one motor configured to drive rotation of the driving wheels.

In some embodiments, the assembly comprises a plurality of transmission gears which transfer torque from the at least one motor to the plurality of driving wheels.

In some embodiments, the driving wheels and the transmission gears are arranged as an elongate construct, wherein the elongate construct is rotatable, as a whole, by at least one gear wheel.

In some embodiments, the transmission gears and the at least one motor drive all of the plurality of pairs of driving wheels at a similar speed of rotation.

In some embodiments, the assembly comprises a plurality of elastic elements coupled to each of the at least one driving wheel of each pair, wherein a change in tension of each of the elastic elements moves the driving wheel between the first position and the second position, wherein the change in tension of the plurality of elastic elements is made simultaneously by movement of a rod which interconnects the plurality of elastic elements.

In some embodiments, the elastic element comprises a spring.

In some embodiments, the assembly comprises between 2-16 pairs of driving wheels.

According to an aspect of some embodiments there is provided a compact robotic device for manipulation of at least one elongate surgical tool, comprising:

a housing including walls which define an inner volume containing:

at least one elongate channel for receiving the at least one elongate surgical tool, the channel having at least one first aperture leading into or out from the housing;

a driving assembly for driving one or both of linear movement and roll movement of the at least one elongate surgical tool, when the at least one elongate surgical tool is received within the channel;

at least one connector in communication with the channel, the connector comprising a branch defining a second aperture located at or externally beyond the walls of the housing, the second aperture being separate from the first aperture of the channel.

In some embodiments, the connector comprises a stem portion which is aligned with the channel, and the branch extends at an angle from the stem portion.

In some embodiments, the branch extends at an angle of less than 90 degrees relative to a long axis of the stem portion which is aligned with a direction of advancement of the at least one elongate surgical tool into a patient body.

In some embodiments, the connector is formed as an integral component of the compact robotic device.

In some embodiments, the walls of the housing at a location of the connector are formed of a transparent material or comprise a window allowing visual access of the connector.

In some embodiments, the device comprises a seal at an attachment between the stem portion and the channel, the seal shaped and configured to allow an elongate surgical tool to pass through and hermetically surround the elongate surgical tool thereby preventing fluid injected through the branch from entering the channel.

In some embodiments, the device comprises a seal located at a proximal portion of the stem portion, the seal shaped and configured to allow an elongate surgical tool to pass through and hermetically surround the elongate surgical tool thereby preventing fluid injected through the branch from entering the channel.

In some embodiments, the branch extends at an angle of more than 90 degrees relative to a long axis of the stem portion containing the seal.

According to an aspect of some embodiments there is provided a compact robotic device for manipulation of at least two elongate surgical tools, the device comprising:

a unitary housing having a tapering cross section profile which narrows in width; the housing defining a first upper portion including a first channel for a first elongate surgical tool and a second lower portion including a second channel for a second elongate surgical tool, wherein a width of the second portion at a position of the second channel is at least 30% smaller than a width of the first portion at a position of the first channel.

In some embodiments, the tapering cross section profile of the housing is defined between an upper end face of the housing and a lower end face of the housing, the first portion including the first channel extending along a length of the upper end face and the second portion including the second channel extending along a length of the lower end face.

In some embodiments, the position of the first channel is 0.1-3 cm away from the upper end face, and the position of the second channel is 0.1-3 cm away from the lower end face.

In some embodiments, a long axis of the first channel is parallel to the upper end face and a long axis of the second channel is parallel to the lower end face.

In some embodiments, a first driving assembly is located in the first portion and configured to operably contact the first elongate surgical tool to advance, retract and roll the first elongate surgical tool; and wherein a second driving assembly is located in the second portion and configured to operably contact the second elongate surgical tool to advance and retract the second elongate surgical tool.

In some embodiments, each of the first and second driving assemblies comprises: at least one motor;

a plurality of movement driving wheels positioned and configured to operably contact the elongate surgical tool;

a plurality of transmission gears for transferring torque from the at least one motor to the plurality of movement driving wheels.

In some embodiments, the first driving assembly further comprises a gear positioned along a long axis of the first driving assembly, the long axis of the first driving assembly being parallel to the upper end face; wherein the gear rotates the first driving assembly as a whole to thereby roll the first elongate surgical tool, wherein rotation of the first driving assembly takes place within the first upper portion.

In some embodiments, a radius of rotation of the first driving is no more than 60% smaller than the width of the first upper portion.

In some embodiments, there is provided a system comprising:

the compact robotic device for example as described hereinabove, and a remote control configured to control operation of the first and second driving assemblies.

In some embodiments, the system comprises a support fixture on which the compact robotic device is removeably mounted.

According to an aspect of some embodiments there is provided a method for controlling linear movement of an elongate surgical tool at least partially received in a designated channel of a compact robotic device, comprising:

positioning the elongate surgical tool at a first position within the designated channel inside the robotic device, wherein at the presence of the elongate surgical tool in the first position is detectable by one or more sensors located at the channel;

positioning the elongate surgical tool at a second position within the channel, wherein at the second position the presence of the elongate surgical tool is not detectable by the one or more sensors; and upon receipt of a command to move the tool linearly along the channel, using the second position for calibrating movement of the tool.

In some embodiments, positioning comprises advancing or retracting the tool along the channel.

In some embodiments, a portion of the tool which is being detected by the one or more sensors comprises one of: a distal end segment of the tool, a proximal end segment of the tool.

In some embodiments, the one or more sensors include optic sensors.

In some embodiments, the method comprises counting, via an encoder, a number of motor rotations required for moving the elongate surgical tool from the first position to the second position, and then using the counted number for automated retraction or advancement of the elongate surgical tool between the first and second positions.

In some embodiments, the automated retraction or advancement is to a third position located a predetermined distance from the first position.

In some embodiments, the automated retraction or advancement is to a third position located a predetermined distance from the second position.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic diagram of a system comprising a compact robotic device for manipulating elongate surgical tools, according to some embodiments;

FIGS. 2A-C are various external views of a compact robotic device for manipulating elongate surgical tools, according to some embodiments;

Figure 5A:
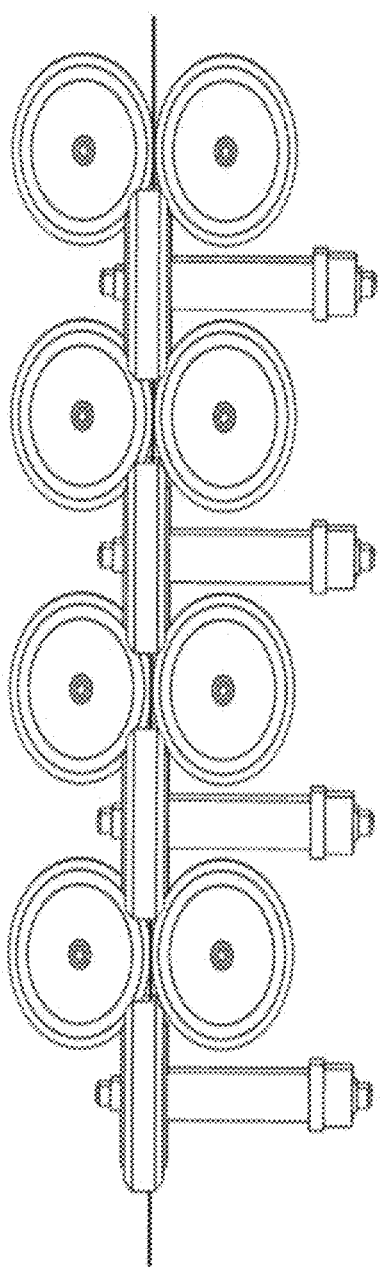
Figure 5B:
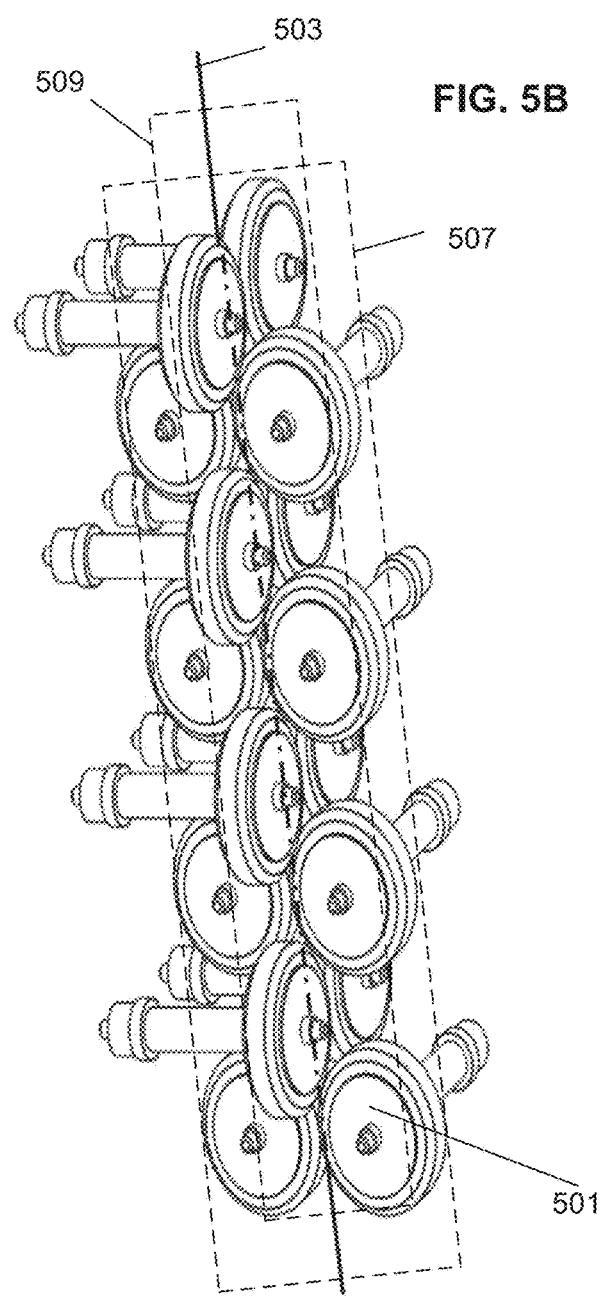
Figure 5C:
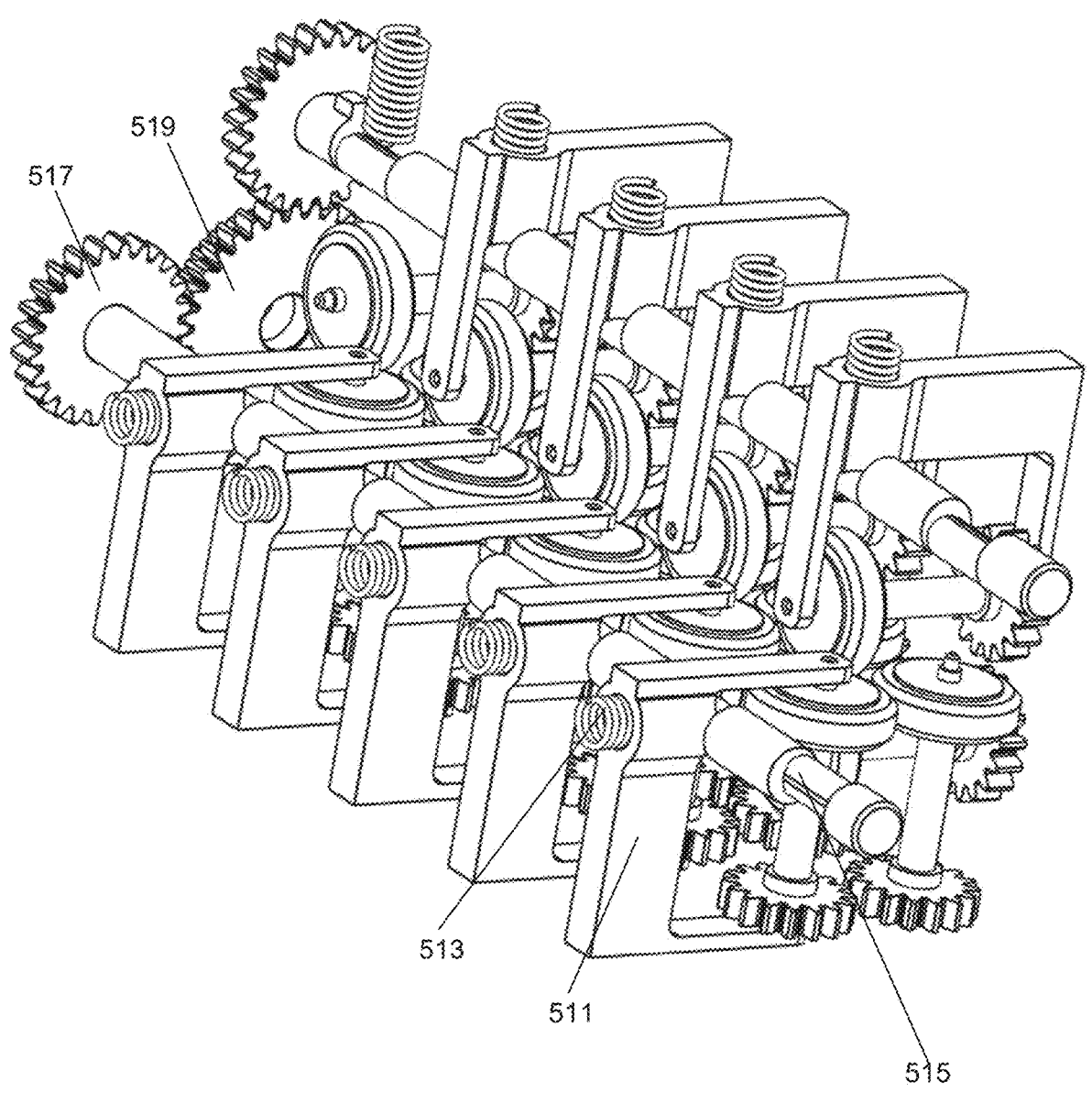
Figure 6A:
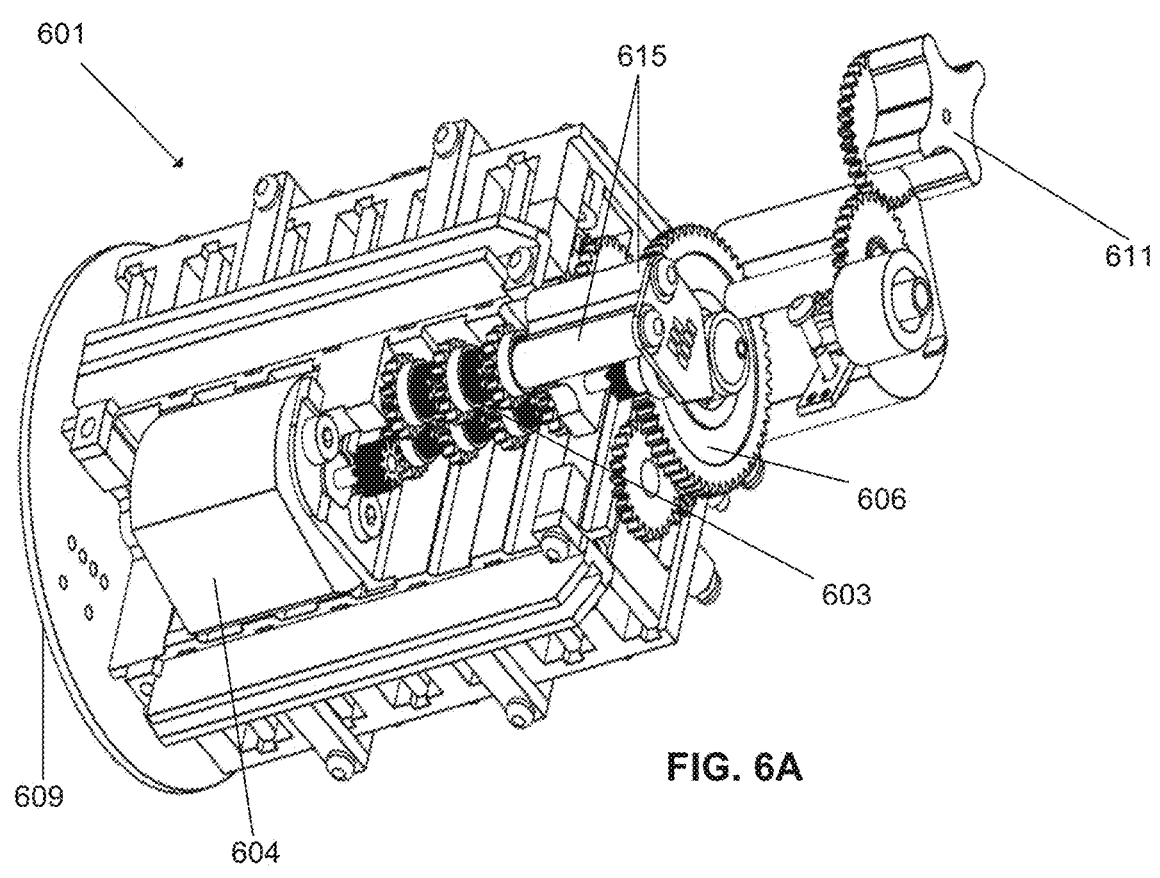
Figure 6B:
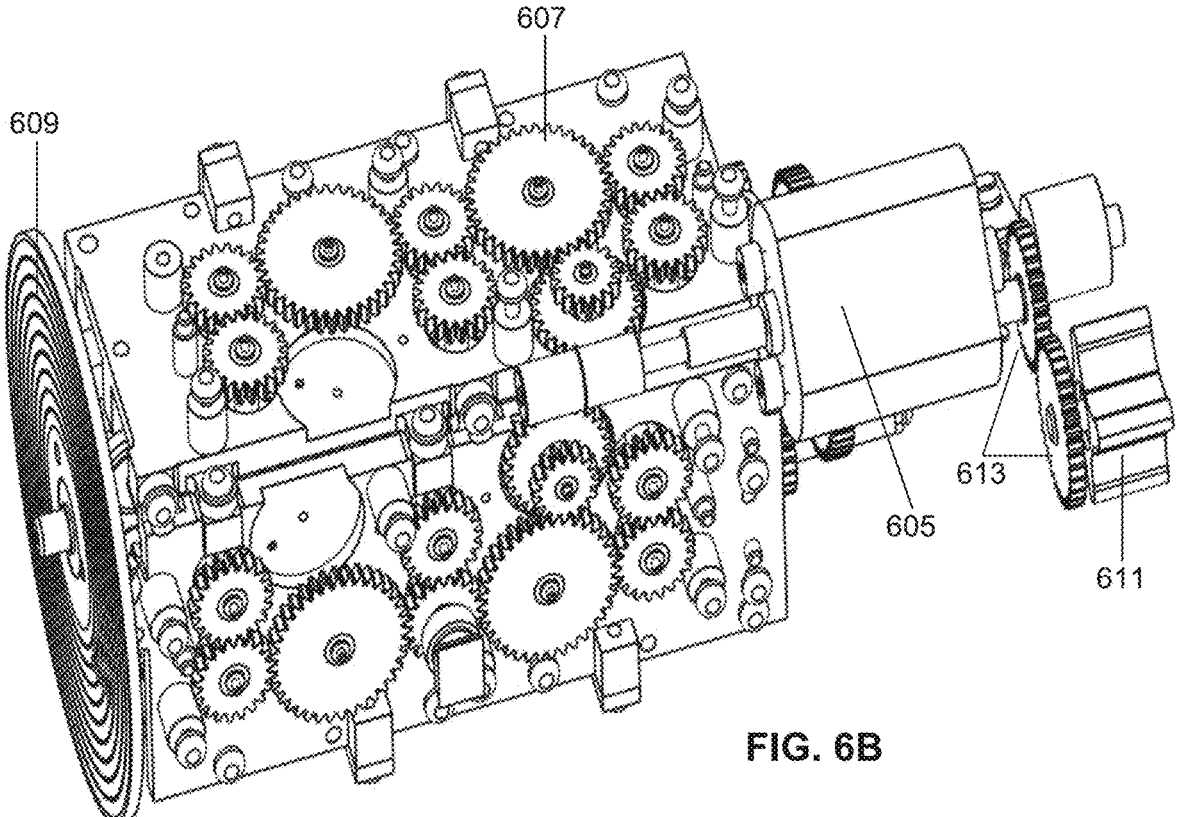
Figures 7A, 7B, 7C:
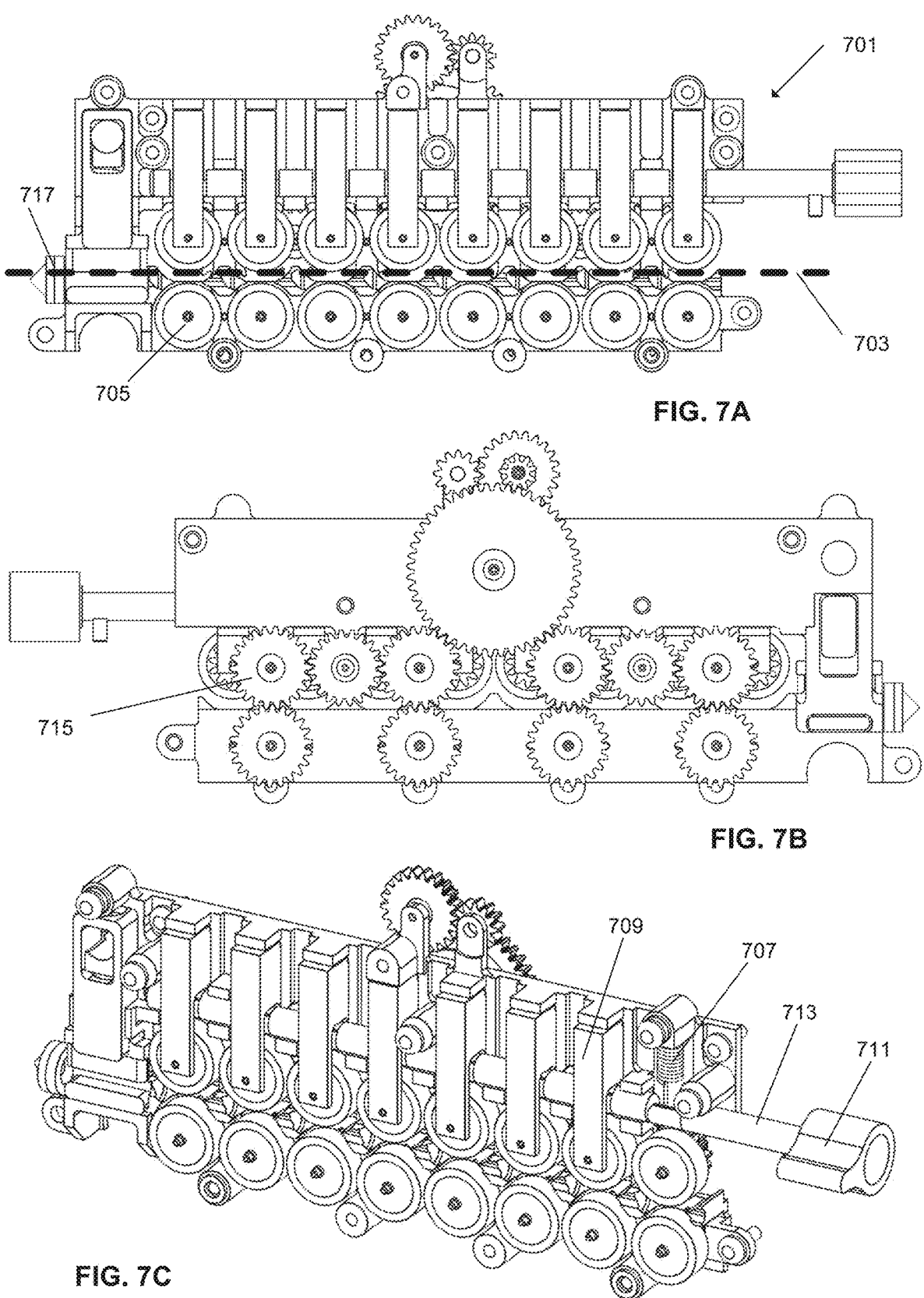
Figure 8:
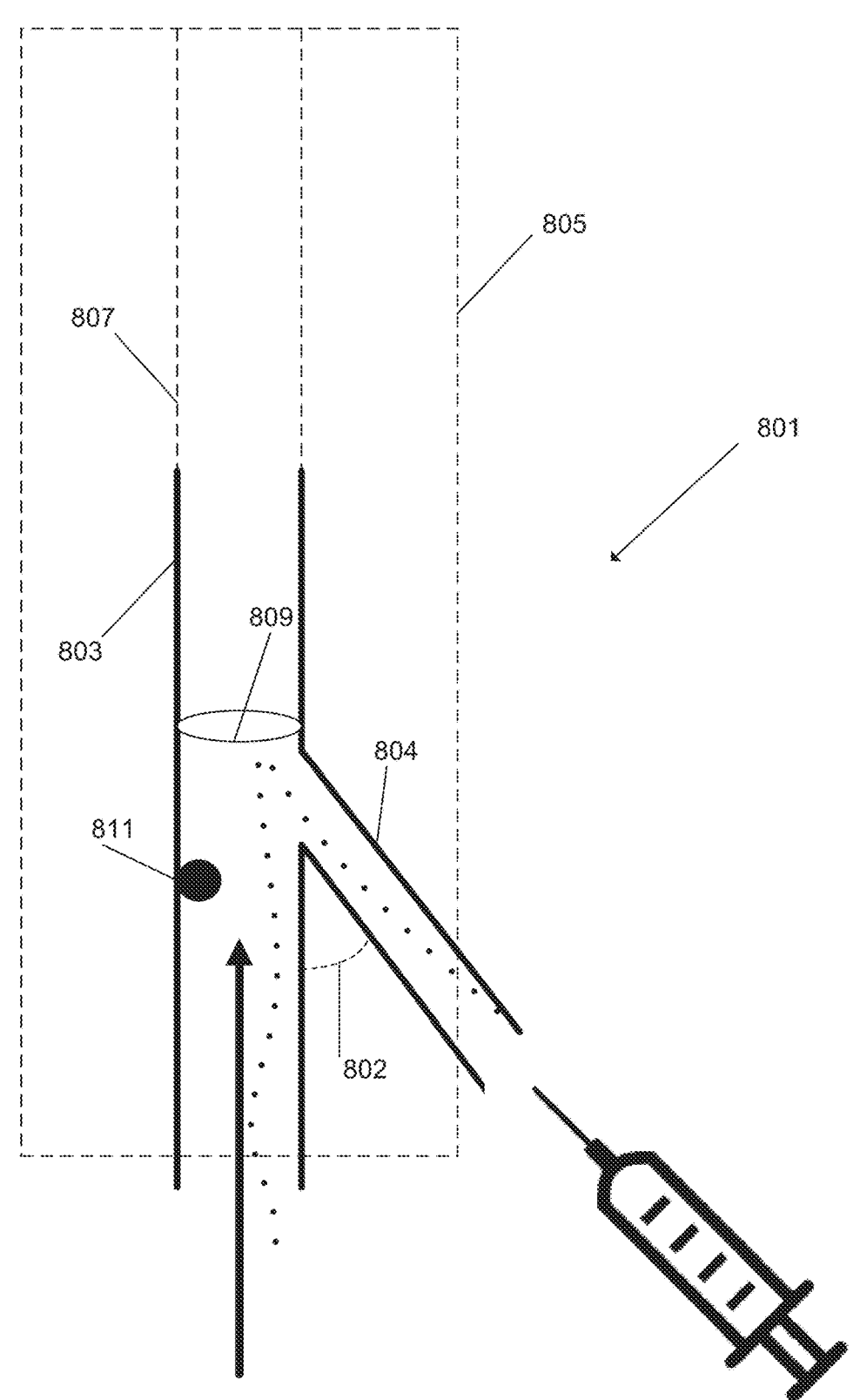
Figures 9A, 9B:
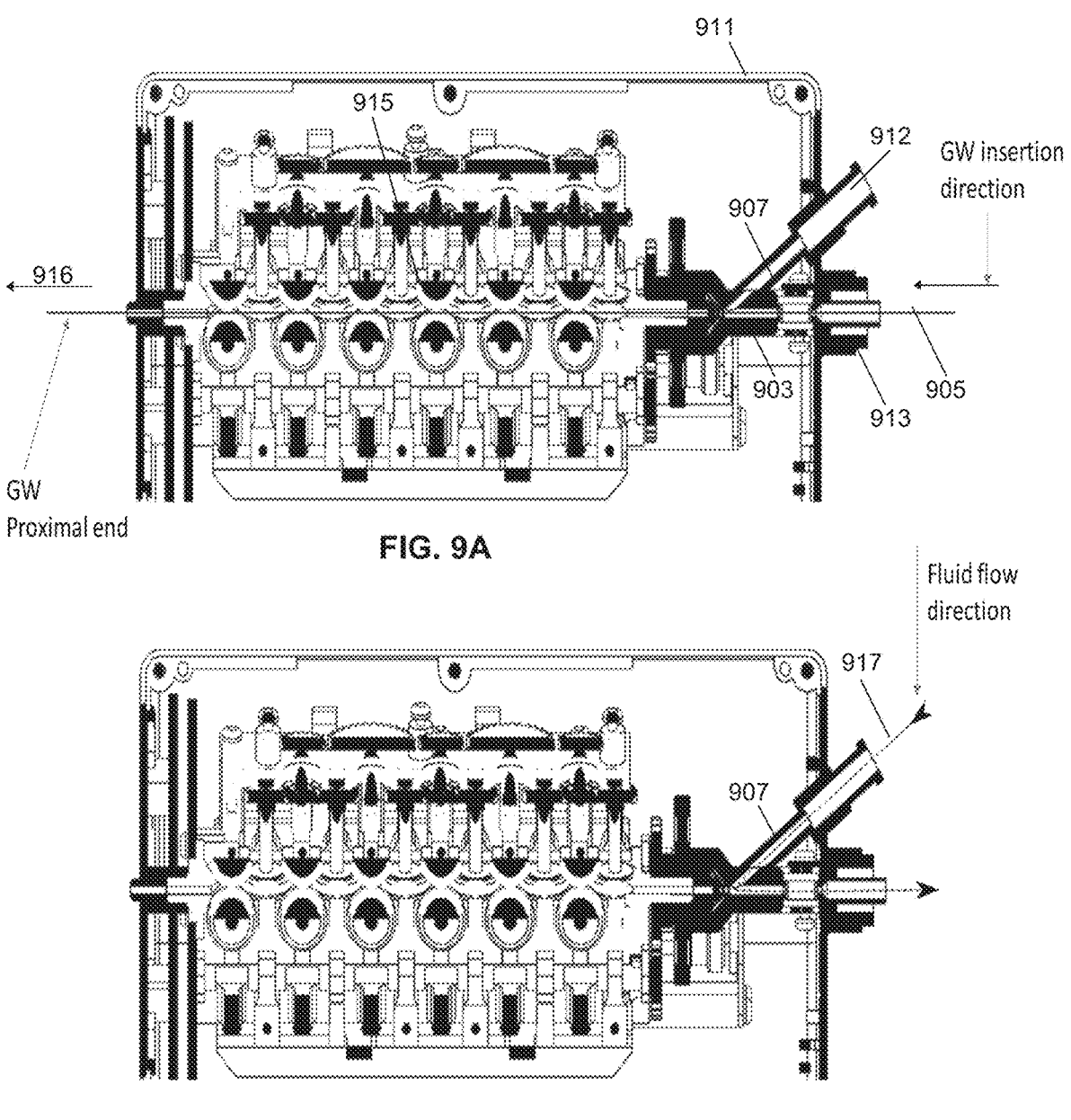
Figure 10A:
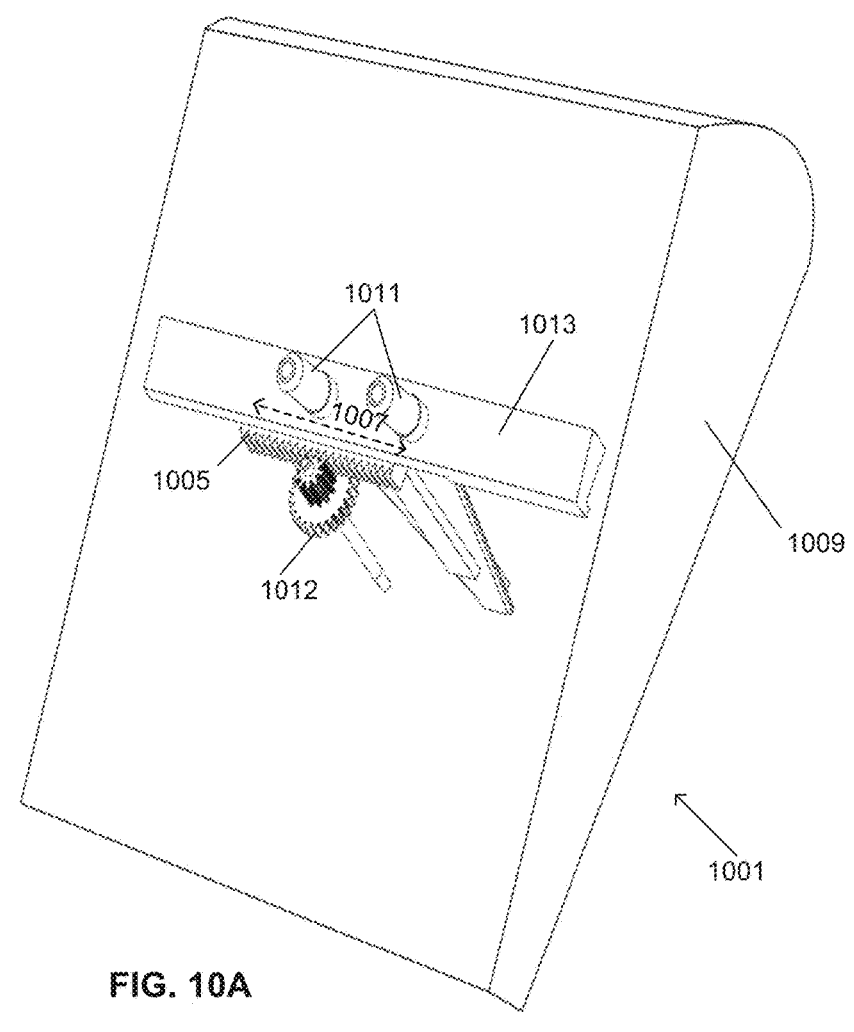
Figure 10B:
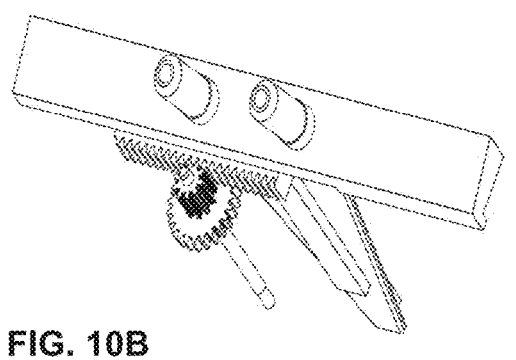
Figure 10C:
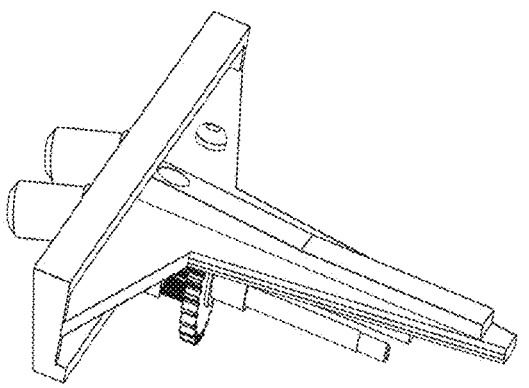
Figure 13:
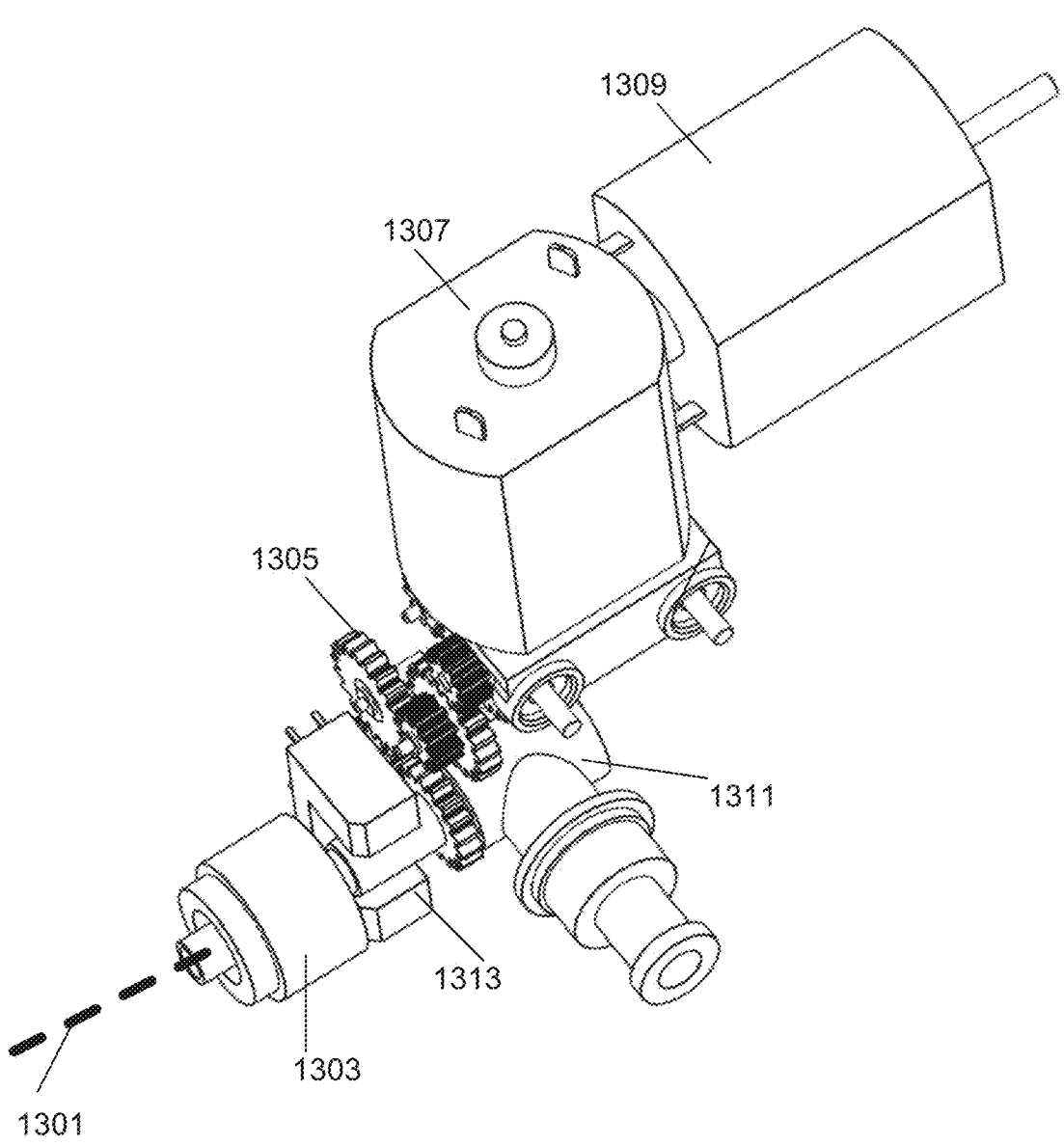
Figure 14:
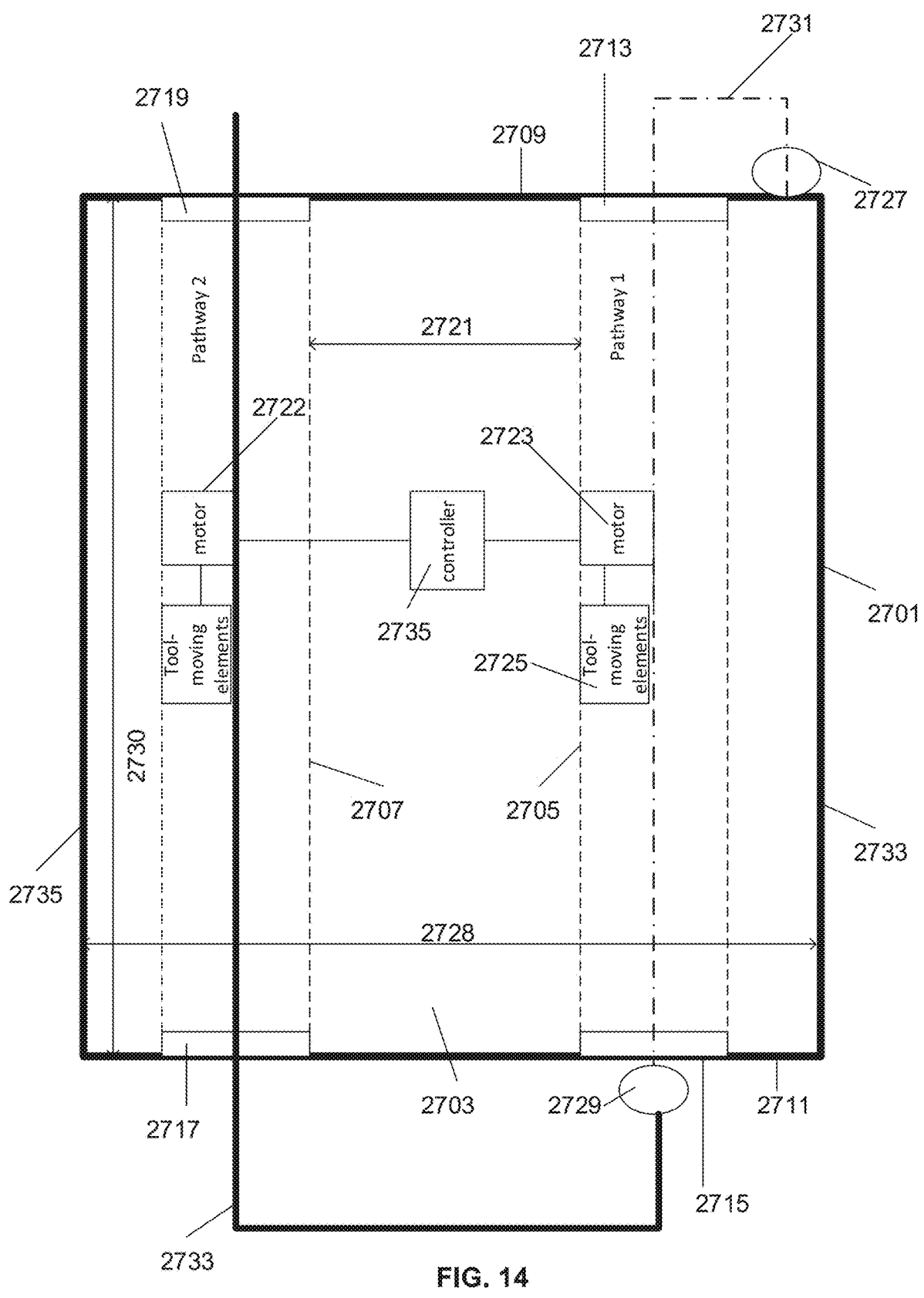
Figure 15:
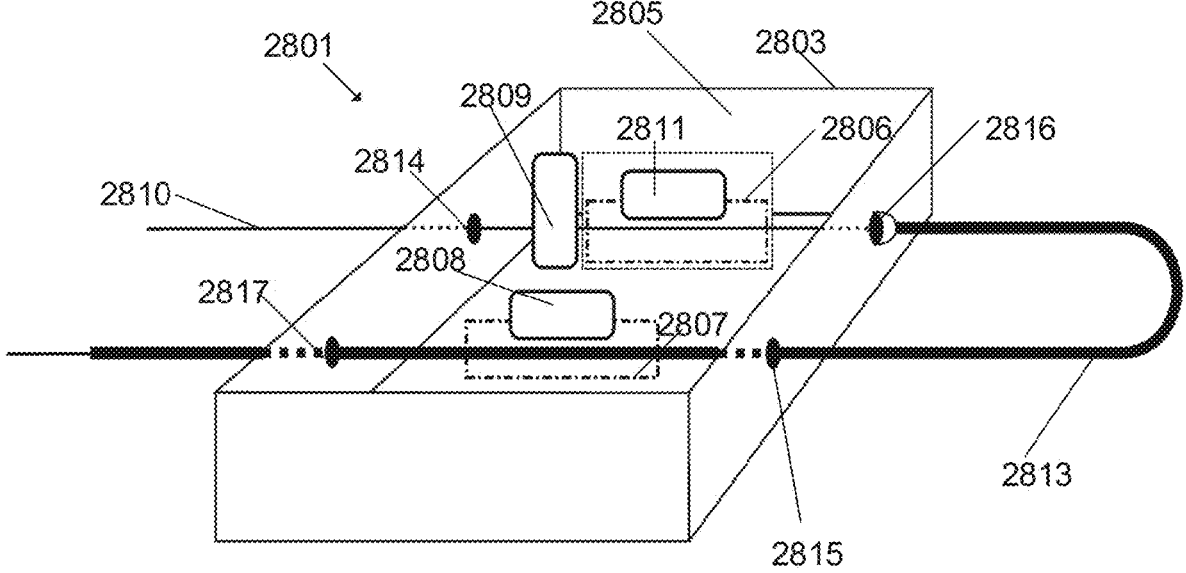
Figure 16:
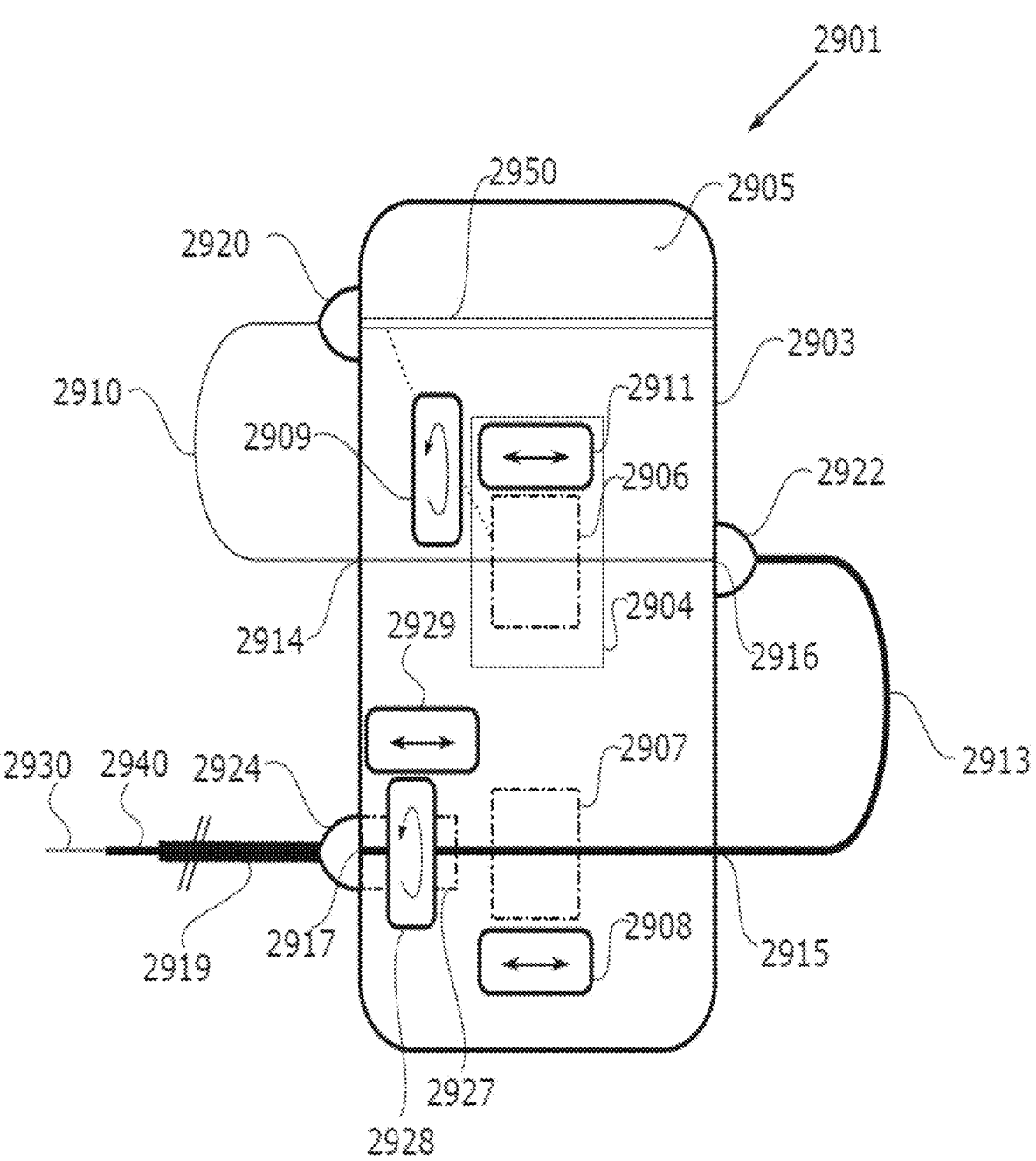

FIGS. 5A-C are different views of a driving assembly for moving a tool, according to some embodiments;

FIGS. 6A-B show a construct for linearly moving and/or rotating a tool, according to some embodiments;

FIGS. 7A-C show an assembly for linearly moving a tool, according to some embodiments;

FIG. 8 is a schematic diagram of a connector which is integral with the device housing, according to some embodiments;

FIGS. 9A-B are internal views of a robotic device comprising an integral connector, according to some embodiments;

FIGS. 10A-C show a rail mechanism for sliding movement of the robotic device together with its assembled tools, according to some embodiments;

FIG. 11A is a flowchart of a method for setting a reference position of an elongate tool in its designated channel of the robotic device, according to some embodiments;

FIGS. 11B-C schematically show different positions of an elongate tool in its designated channel, according to some embodiments;

FIG. 12 is a flowchart of a method for loading elongate surgical tool(s) onto the compact robotic device, according to some embodiments;

FIG. 13 is an example of an assembly for coupling a guiding catheter to the compact robotic device and for moving the guiding catheter using the compact robotic device, according to some embodiments;

FIG. 14 is a schematic block diagram of a robotic device configured for manipulating two or more elongate surgical tools, according to some embodiments;

FIG. 15 schematically illustrates a robotic device for manipulation of a guidewire and a microcatheter, the guidewire extending at least in part within the microcatheter lumen, according to some embodiments; and FIG. 16 schematically illustrates a robotic device for manipulation of three or more elongate surgical tools configured for a telescopic arrangement, according to some embodiments.

DESCRIPTION OF SPECIFIC EMBODIMENTS OF THE INVENTION

The present invention, in some embodiments thereof, relates to devices and assemblies for robotic manipulation of elongate surgical tools and, more particularly, but not exclusively, to compactly arranged and packed mechanisms for linearly moving and/or rolling an elongate surgical tool.

An aspect of some embodiments relates to a driving assembly for driving movement of an elongate surgical tool, the driving assembly comprising a plurality of pairs of driving elements such as driving wheels where at least one of the pairs lies on a plane different than at least one other plane on which a different, optionally adjacent wheel pair lies.

In some embodiments, the wheel pairs are arranged on at least a first plane and a second plane, the first plane crossing the second plane. Optionally, the first and second planes are perpendicular to each other. Optionally, the wheels pairs are interveningly disposed such that a first pair of wheels lies on the first plane, a second pair of wheels lies on a second plane, a third pair of wheels lies on the first plane, a fourth pair of wheels lies on the second plane, and so forth. In some embodiments, each pair of wheels defines a space therebetween, and the plurality of wheels pairs are arranged about a similar long axis so that the plurality of spaces form an elongate channel for receipt of an elongate surgical tool (e.g. a guidewire). When the elongate surgical tool is received within the channel, the driving wheels contact the tool at a plurality of locations along the length of the tool, so that when the driving wheels are rotated, the tool is caused to move linearly (e.g. be advanced or retracted along the channel).

Some potential advantages of a driving assembly in which the driving wheels pairs are intervened and lie on two planes that cross each other may include: having multiple driving wheels contact the tool at multiple locations along its length, without the wheels spatially interfering with each other, also during rotation of the wheels; enhancing grip of the tool by having multiple wheels pairs contact the tool and hold the tool between opposing wheels of each of the pairs, potentially reducing a risk of slippage of the tool and improving traction; having multiple wheels pairs fitted within a substantially small volume surrounding the tool, potentially allowing for a minimally sized, compact assembly.

In some embodiments, a distance between opposing wheels of each pair is adjustable, for example so that the elongate channel defined between the plurality of wheel pairs can be widened or narrowed. In some embodiments, wheels on at least one side of the channel are coupled to elastic elements, such as springs, and upon a change in tension on the springs, the wheels are moved closer or further away from their opposing wheels (on the other side of the channel). In some embodiments, changes in tension on the springs is simultaneously performed on the two planes of wheels pairs, such that distances between opposing wheels in all the wheels pairs are adjusted. Optionally, this simultaneous operation is executed using a single knob.

In some embodiments, the driving wheels of the driving assembly are actuated by a motor. In some embodiments, a plurality of transmission gears are positioned and configured to transfer torque from the motor to the driving wheels, while optionally adjusting a speed of rotation dictated by the motor. In some embodiments, the driving wheels, transmission gears and the motor form together a construct housed inside a robotic device for example as described herein. In some embodiments, the construct is coupled to a gear or wheel which when rotated rotates the construct as a single unit, thereby causing the elongate surgical tool received within the channel to roll about the tool long axis. In this manner, linear movement of the tool may be carried out via rotation of the driving wheels of the driving assembly, and roll movement of the tool may be carried out via rotation of the construct as a whole.

In some embodiments, a driving assembly acts as a manipulator of the tool, and is configured to move the tool, for example, advance and/or retract the tool, roll the tool.

An aspect of some embodiments relates to a compact robotic device for manipulation of elongate surgical tools which includes an integrally formed connector at least partially contained within a housing of the device. In some embodiments, the connector serves for introducing of a tool through and/or for injection of fluid (e.g. saline, water, medication) into and optionally through a lumen of a surgical tool loaded onto the device. Optionally, the fluid is introduced into the patient body via the lumen of the tool.

In some embodiments, an aperture leading into a lumen of the connector is defined at a wall of the housing (or protrudes from the housing). In some embodiments, the connector aperture is formed separately from at least one aperture leading into and/or out of an elongate channel of the device in which the surgical tool is received.

In some embodiments, the connector includes a stem portion which is axially aligned with the elongate channel; and one or more branches extending at an angle from said stem portion, and optionally at least partially protruding out of the device housing so that the aperture leading into the branch is accessible from outside the housing, enabling the injection of fluids and/or tools into the branch.

In some embodiments, due to the axial alignment of the stem portion and the channel, a tool introduced into the stem portion can be simply advanced, without further navigation of the tool, into the lumen of the channel (or vice versa—a tool introduced into the channel can be directly advanced into stem portion).

In some embodiments, the connector includes a seal, for example located at an attachment between the channel and the stem portion, so that fluid entering via the branch is forced to turn around when reaching the seal, to optionally then flow into a lumen of a tool (such as a microcatheter) which is optionally coupled to the device at an end of the stem portion. In some embodiments, the seal is shaped to allow a tool to pass through, while hermetically surrounding the tool to prevent from fluid from passing. Additionally or alternatively, a seal is located at a proximal portion of the stem portion, allowing the tool to pass through yet preventing the passing of fluid.

Some potential advantages of a connector for example as described which is a part of the robotic device and is optionally contained, at least in part, inside the device housing may include: reducing or avoiding the need to manually attach a connector to the tool (such as before the procedure); potentially facilitating injection of materials into the connector as the connector is firmly held by the device housing; "saving" effective tool length, for example by having the connector extend directly from the channel, for example as compared to a connector that is attached further along the length of the tool, causing "waste" of the tool section extending between the device and the external connector.

An aspect of some embodiments relates to controlling linear movement of a tool in a designated channel of a robotic device by setting a reference location for the tool along the channel. In some embodiments, using one or more sensors such as optic sensors positioned along the channel, a tool position is monitored at least twice: once when the tool reaches (for example, is advanced to) a position in which its presence is detected by the sensors, and once when the tool is moved (e.g. retracted or advanced) to a second position in which its presence is no longer detectable by the sensors. In some embodiments, the second position is used a reference location, for example according to which additional movements of the tool, optionally, automated movements, are carried out, using the reference location for calibration purposes. In some embodiments, a number of motor rotations required for moving the tool between the first and second positions is counted, e.g. via an encoder, and that number is used for further control of the tool, for example when automatically retracting or advancing the tool between the two positions.

Retraction and advancement of tools, such as guidewires, are steps that may be performed many times during a single procedure. For example, when contrast agent is to be injected through the lumen of a microcatheter, the guidewire is first retracted from the microcatheter lumen to allow room for the contract agent to pass through, and once the injection is complete, the guidewire may be re-introduced into the microcatheter for continuing the procedure. A potential advantage of automatic retraction and/or advancing of the tool between two positions may include reducing the amount of time required for these actions, for example as compared to manual advancement/retraction. Automated movement of a tool, such as between two defined positions or along a predetermined distance relative to one of the two positions, may potentially save time for the overall procedure and specifically time of exposure to radiation (such as due to imaging being carried out simultaneously). In such cases, as opposed to manual retraction and advancement, automation keeps the tools set in place and/or accurately transfers the tools between positions. Therefore, using automation can be done very fast, and substantially without risk of unwanted movements, for example as compared to manually operated movement.

An aspect of some embodiments relates to a compact robotic device which accommodates driving assemblies for elongate surgical tools, where the device housing comprises a tapering profile which narrows in width, being shaped and sized to specifically match movement and size of the driving assemblies therein. In some embodiments, the device comprises a unitary housing, where an upper portion of the housing accommodates a construct for example as described herein which is structured for linear movement and roll of an elongate tool, such as a guidewire; and a lower portion of the housing accommodates a driving assembly structured solely for linear movement of a tool, such as a microcatheter. In some embodiments, the wider upper portion is sized so that the construct can rotate, as a whole, inside the device housing (such as for generating roll of the guidewire).

A potential advantage of a device having a tapering cross section profile, where walls of the device housing closely fit the assemblies contained inside, may include a minimally sized, compact device, which potentially reduces interference in the surgical room setting and potentially facilitates maneuvering of the device and/or positioning of the device relative to the patient and/or surgical bed.

As referred to herein, the term "distal" may refer to device and/or surgical tool portions which are closer to the patient, for example, closer to an entry point into the patient body, or closer to a target location which is being operated on inside the patient body; the term "proximal" may refer to device and/or surgical tool portions which are further away from the patient. The terms "upper" and "lower" are used herein as relative terms with respect to the device structure, for example, to more clearly define the shape of the device housing, and should not be construed as limiting with regards to a position of the device with respect to the surgical bed and/or the patient. It is noted that the device is positionable at any selected position and orientation which facilitates insertion of the surgical tools into the patient body and/or facilitates manipulation of the tools via the device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Compact Robotic Device

Figure 1:
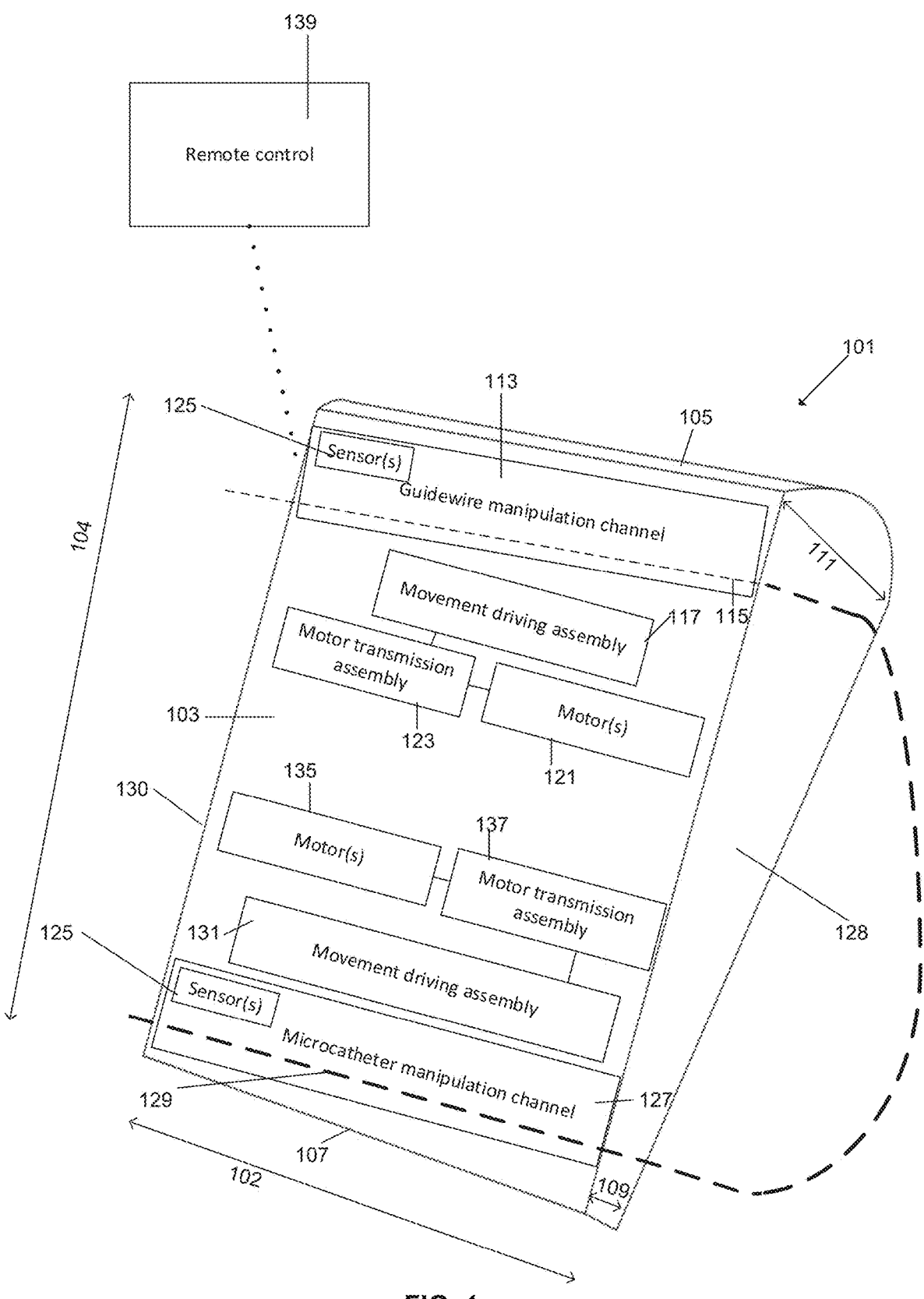

Referring now to the drawings, FIG. 1 is a schematic diagram of a system 100 comprising a compact robotic device for manipulating elongate surgical tools, according to some embodiments.

In some embodiments, device 101 is configured to manipulate elongate surgical tools configured to be introduced into a body of the patient, such as a guidewire, a microcatheter, an intermediate catheter, a guiding catheter. In some embodiments, the tools are telescopically arranged, for example one tool is at least partially insertable into a lumen of another.

In some embodiments, the device is configured for use in a surgical room setting, and may be used, for example, in operations involving insertion of one or more tools into and/or through vasculature and/or into other non-vascular endoluminal structures. In some embodiments, the operation involves catheterization. In some embodiments, the operation involves a through-lumen based procedure. In some embodiments, the operation involves an over-the-wire based procedure.

In some embodiments, the device is constructed so that no shielding (e.g. no physical separation by a wall, a wrap, a drape) exists or is required between components housed within the device and the one or more tools that are loaded onto the device, for example, such that direct contact is formed between the tool and at least some of the device components (e.g. wheels, gears, and/or other actuators). Optionally, no draping by a sterile drape or other cover is required. In some embodiments, the device is a single-use device that is disposed following surgery.

In some embodiments, device 101 comprises a housing 103 which is shaped and sized to be small enough so as to reduce spatial interference, for example to reduce or prevent visual and/or physical obstruction and/or reduce interference while accessing the patient.

In some embodiments, a volume of the device, optionally including the housing, is less than 2500 cm^3.

In some embodiments, the housing comprises a tapering profile which decreases in width between an upper end face 105 of the housing and a lower end face 107 of the housing. In an example, a shortest width 109 of the housing is at least 30%, at least 50%, at least 70% or intermediate, larger or smaller percentage shorter than a maximal width 111 of the housing.

Exemplary device dimensions may include an axial length 102 of between 8-20 cm, a height 104 of between 8-20 cm, and a width which varies from 8-12 cm at a maximal width 111 and 2-6 cm at a minimal width 109.

In some embodiments, the housing accommodates a plurality of channels in which a corresponding plurality of elongate surgical tools are received.

In some embodiments, as shown, an upper portion of the device includes a channel 113 for manipulation of a tool, such as a guidewire 115. In some embodiments, a movement driving assembly 117 of channel 113 is configured and positioned to move the guidewire received within the channel. For example, assembly 117 comprises a plurality of driving wheels and/or gears which come in contact with the guidewire to move it. In some embodiments, assembly 117 is configured for linearly moving the guidewire (retracting and/or advancing the guidewire along a long axis of channel 113) and/or for rolling the guidewire about the guidewire long axis.

In some embodiments, movement driving assembly 117 is actuated by one or more motor(s) 121, where a motor transmission assembly 123, for example comprising a plurality of gears, transfers torque from the motor(s) to the assembly. In some embodiments, transmission assembly 123 is configured to modify (reduce or increase) the actuation speed provided by motor(s) 121 and to drive movement of movement driving assembly 117 at a selected speed or speed range.

In some embodiments, roll of the guidewire is carried out by rotation of channel 113 along with the movement driving assembly 117, and optionally along with the motor transmission assembly 123 and the motor(s) 121. In some embodiments, the assemblies and motor(s) together form a construct which rotates as a unitary piece which thereby rolls the guidewire that is held within the channel by the movement driving assembly.

In some embodiments, rotation of such construct as a whole is enabled due to the wider profile of the housing at the upper portion of the housing. In some embodiments, rotation of the construct as a whole is enabled due to the lack of a sterile drape between the rotated components and the actuating motor.

In some embodiments, as shown, a lower portion of the device includes a channel 127 for manipulation of a tool, such as a microcatheter 129. In some embodiments, a movement driving assembly 131 of channel 127 is configured and positioned to move the microcatheter received within the channel. For example, assembly 131 comprises a plurality of driving wheels and/or gears which come in contact with the microcatheter to move it. In some embodiments, assembly 131 is configured for linearly moving the microcatheter (retracting and/or advancing the guidewire along a long axis of channel 127).

In some embodiments, movement driving assembly 131 is actuated by one or more motor(s) 135, where a motor transmission assembly 137, for example comprising a plurality of gears, transfers torque from the motor(s) to the assembly. In some embodiments, transmission assembly 137 is configured to modify (reduce or increase) the actuation speed provided by motor(s) 135 and to drive movement of movement driving assembly 131 at a selected speed or speed range.

In some embodiments, the channels for receipt of tools which are defined inside the device, such as channel 113, channel 127, extend between opposing walls of the device housing, such as between a proximal face 128 of the housing and a distal face 130 of the housing.

In some embodiments, a width of the housing at a position of channel 115 (e.g. at a distance of between 1 mm-50 mm from the upper face 105) is at least 40%, 60%, 80% or intermediate, larger or smaller percentage larger than a width of the housing at a position of channel 127 (e.g. a distance of between 1 mm-50 mm from the lower face 107).

In some embodiments, the device comprises one or more sensors 125, such as sensors for detecting parameters such as: presence of a tool, a direction of movement of a tool, a speed of movement of a tool, motor speed, rotational orientation (e.g. of a construct as described above).

In some embodiments, one or more sensors are located along one or both channels 113, 127.

In some embodiments, the device further comprises an assembly for manipulation of a guiding catheter (not shown). In some embodiments, the guiding catheter manipulation assembly is configured in the lower portion of the device. Optionally, the guiding catheter attaches to the device externally to the housing. In some embodiments, linear movement of the guiding catheter is driven by movement of device 101 as a whole, for example along a rail mechanism as further described herein.

In some embodiments, system 100 comprises a remote control 139 through which a user (e.g. surgeon or other medical personnel) controls manipulation of tools by the device. In some embodiments, remote control 139 is operated remotely from device 101, at a distance from it. In an example, the remote control is operated from a different room. Alternatively, the remote control is operated at the surgical room. In some embodiments, the remote control is programmed to send signals and/or receive signals from device 101, for example to actuate tool movement (e.g. linear movement and/or rotation of the one or more tools loaded onto the device).

In some embodiments, system 100 may further include an imaging device, or used in conjunction with an imaging device, such as X-ray fluoroscopy, CT, cone beam CT, CT fluoroscopy, MRI, ultrasound, or any other suitable imaging modality.

FIGS. 2A-C are various external views of a compact robotic device for manipulating elongate surgical tools, according to some embodiments.

In some embodiments, device 201 comprises a housing 203 which defines access apertures leading into a volume inside the housing, apertures leading outside the housing, and optionally one or more protrusions (e.g. knobs) which protrude from the walls of the housing and may be engaged externally to the housing, such as manually by a user and/or via additional device(s).

In the example shown in FIG. 2A, the device is loaded with a guidewire 205, a microcatheter 207 through which the guidewire is introduced, and a guiding catheter 209 through which the telescopic arrangement of the guidewire and microcatheter is introduced.

In some embodiments, the guidewire is received within a designated channel on an upper portion of the device (channel is internal and not shown), and extends (optionally, advanced) into a lumen of the microcatheter which in turn is connected at its proximal end to the housing 203, for example, via a luer 211. The microcatheter then extends to form a curve 213 outside the housing, for example, a U-shaped curve, and enters the inner volume of the device at aperture 215, which is located at a lower portion of the device. Inside the housing, the microcatheter (optionally including the guidewire threaded therein) extends along its designated channel (channel is internal and not shown). The microcatheter then exits the housing at luer 217, where, optionally, a proximal end of the guiding catheter 209 is attached, and the microcatheter enters the lumen of the guiding catheter.

In some embodiments, housing 203 includes one or more ports leading into a lumen of a tool, for example for injection of fluid (e.g. saline) into and through the tool. For example, port 219 forms a branch of an inner connector which leads into a lumen of the microcatheter; port 221 forms a branch of another inner connector which leads into the lumen of the guiding catheter. In some embodiments, in use, fluid is injected into the port and is directed by the connector to flow into the lumen of the tool.

In some embodiments, housing 203 includes one or more protrusions (e.g. pins, buttons or knobs) which extend from the inner volume of the device externally to the housing so that upon being engaged (e.g. manually engaged by a user, and/or automatically, such as via a designated motor, an external actuator, and/or other their movement generates movement of inner components of the device. For example, rotation of a knob 223 located on the device upper portion releases grip of the guidewire, for example by compressing one or more elastic elements (e.g. springs) to thereby distance elements of a movement driving assembly (e.g. wheels) which are coupled to the springs away from the guidewire. In a similar manner, rotation of a knob 225 located on the device lower portion releases grip of the microcatheter, for example by compressing one or more elastic elements (e.g. springs) to thereby distance elements of a movement driving assembly (e.g. wheels) which are coupled to the springs away from the microcatheter.

In some embodiments, one or more pins 227 protrude from the walls of the housing for attachment of the device to a support and/or to a rail mechanism.

In some embodiments, in use, roll movement of the guidewire is carried out by rotation of an inner construct (which includes the movement driving assembly and the motor transmission assembly). Rotation of the construct is in some embodiments visible externally to the housing as rotation of disc portion 229, configured on the wider upper portion of the device.

In some embodiments, the device is configured to provide visible and/or audible and/or tactile indications to a user, for example for indicating a current position and/or movement of a loaded tool. For example, in some embodiments, the housing comprises a series of lights (e.g. LEDs) which light up in a timing and an order which matches movement of a tool, for example, advancement or retraction of a tool along its designated channel. Optionally, the device includes at least a first series of lights configured externally on the walls housing at a location of the guidewire channel, and a second series of lights configured externally on the walls housing at a location of the microcatheter channel, for indicating linear movement of each of these tools.

Additionally or alternatively, is some embodiments, an external indicator device is provided for use by a user which remotely controls manipulation of the tools by the device. In some embodiments, the indicator device indicates movement of the tool(s) loaded onto the robotic device (e.g. linear movement, roll) to a user, via a visible indication (e.g. screen, lights) and/or an audible indication and/or a tactile indication. Such device may be configured as a hand held device, as a cellular phone application for installation by a user, as an add-on device (for example mountable onto a remote control of the robotic device and/or onto a screen), and the like. Optionally, the indicator device is located remotely to the robotic device, for example positioned in a room different than the surgical room, from which control of operation is carried out.

Exemplary Surgical Room Setup

Figure 3:
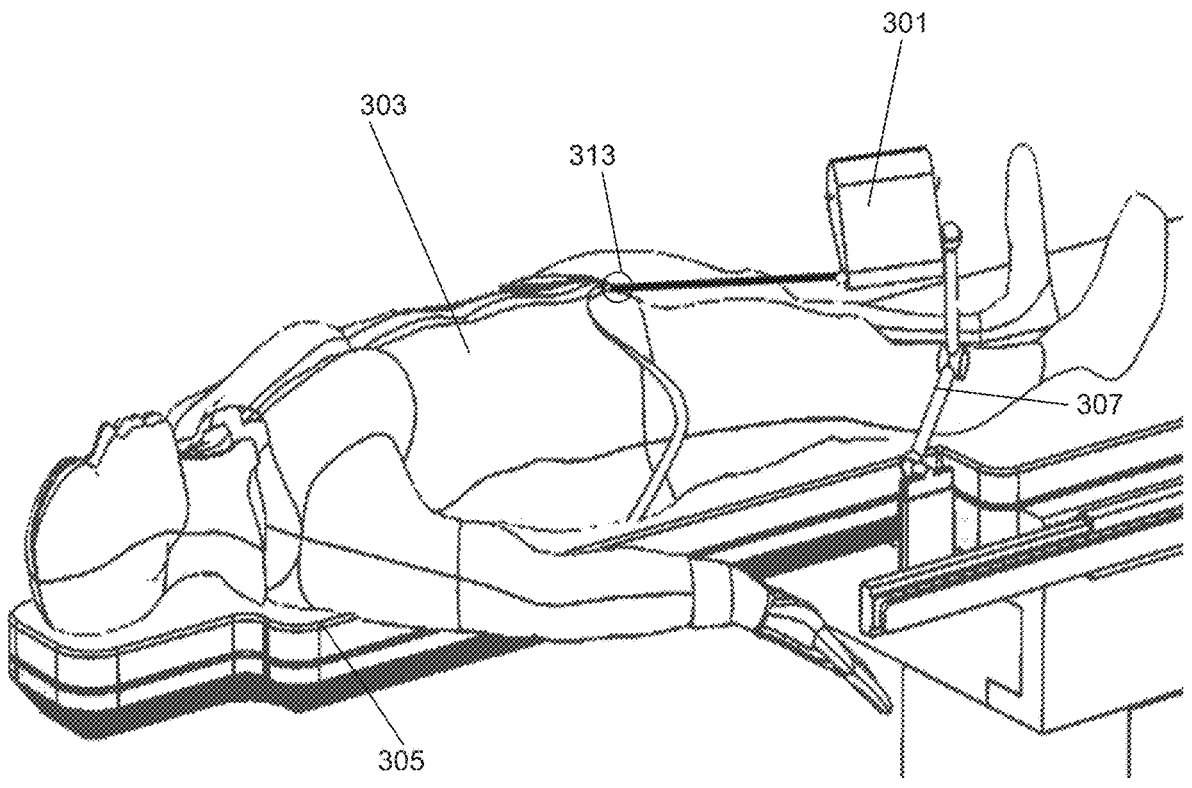
FIG. 3 is an example of a surgical room setup for a compact robotic device, according to some embodiments.

FIG. 3 is an example of a surgical room setup for a compact robotic device, according to some embodiments. In some embodiments, the compact robotic device 301 is positioned and held with respect to a patient 303 lying on the surgical bed 305. In some embodiments, the device is removably mounted onto a distal end of a support fixture 307 which is optionally fixed, at its proximal end, to the bed 305.

In some embodiments, support fixture 307 allows to set a position of device 301 relative to the patient, for example, relative to an entry point 313 for insertion of the one or more elongate surgical tools into the patient's body.

In some embodiments, depending on the location of the target tissue (for example, the heart, a peripheral blood vessel in the lower extremities, brain, liver, and the like) and the purpose of the procedure, the entry point may be selected from, but not limited to, at the patient's groin (i.e., the femoral artery), arm (i.e., the radial artery) or neck (i.e., the jugular vein). In some embodiments, the tool(s) are introduced into a blood vessel lumen.

In some embodiments, device 301 is attached to the support fixture via an interference fit coupling, e.g. by one or more pins received within respective recesses, and/or other suitable coupling.

In some embodiments, device 301 is configured to move relative to the support fixture 307, for example, by sliding on a rail. In some embodiments, the rail is comprised within and/or mounted on the housing of the robotic device itself, for example as shown in FIGS. 10A-C. Additionally or alternatively, the rail forms a part of the support fixture.

In some embodiments, following operation, both device 301 and support fixture 307 are disposed of. Alternatively, the support fixture is configured for multiple uses, for example, by sterilizing the fixture following use.

In some embodiments, device 301 is positionable at any selected orientation relative to the patient, for example at an orientation which most effectively reduces interference with visualization (optionally by imaging) and/or with physical access to the patient (such as for introducing of tools). In some embodiments, device 301 is mounted on the fixture such that the narrow portion (also referred to herein as bottom portion) of the device is closer to the entry point into the patient body, so that a tool or a telescopic arrangement of tools (e.g. a microcatheter and a guidewire extending within) exit device 301 at a location closest to entry point to the body.

Tool Manipulation Assemblies

Figure 4:
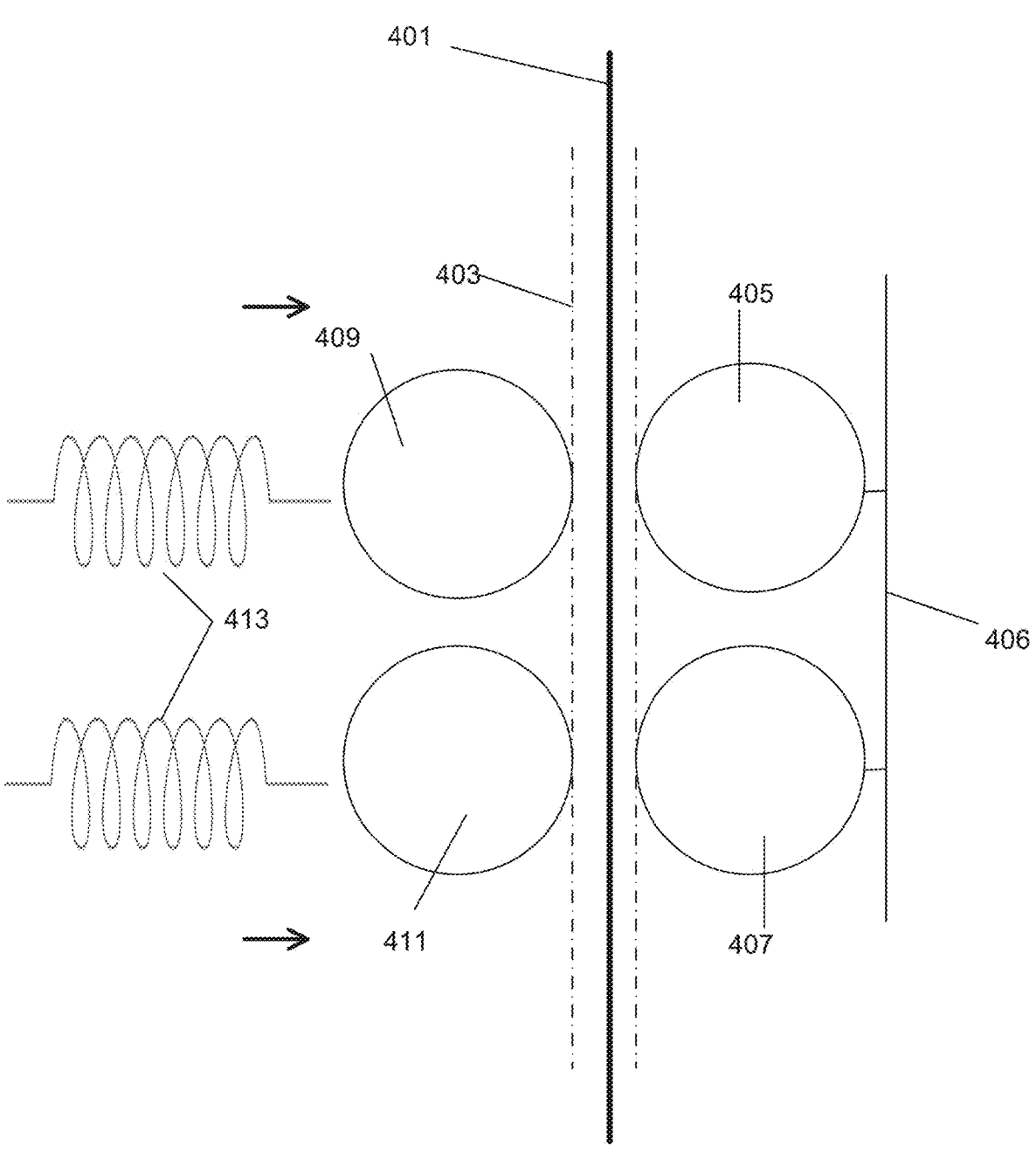
FIG. 4 is a schematic diagram of a driving wheel assembly for linearly and/or rotationally moving an elongate surgical tool, according to some embodiments.

FIG. 4 is a schematic diagram of a driving wheel assembly for linearly and/or rotationally moving an elongate surgical tool, according to some embodiments.

In some embodiments, an elongate surgical tool 401 (e.g. a guidewire, a microcatheter) is received within a designated channel 403 of the device.

In some embodiments, a plurality of movement driving elements such as driving wheels are positioned adjacent the channel. In some embodiments, the wheels are arranged in pairs where one wheel is opposite another wheel which is located across the channel. The movement assembly may include, for example, between 2-40 wheels, such as 10-20, 8-16, 4-30, 12-38 or intermediate, larger or smaller number of wheels.

In some embodiments, wheels on a first side of the channel (such as wheels 405, 407) are coupled to a stationary element 406 (e.g. an inner wall of the housing, a frame, a rod and the like). In some embodiments, wheels in a second opposing side of the channel (such as wheels 409, 411) are coupled to elastic or deformable elements, such as springs 413.

In some embodiments, in a rest state of the springs, wheels 409, 411 are pushed by the springs in close proximity to wheels 405, 407 such that the tool 401 is contacted by all wheels. Upon rotation of the wheels, the tool is advanced or retracted (depending on the direction of rotation of the wheels) along a long axis of the channel. In some embodiments, in the approximated state of the wheels, the opposing wheels of each pair are brought to a distance which is equal to or shorter than a diameter of tool 401, for example, equal to or shorter than a diameter of a guidewire, e.g. a guidewire diameter between, for example, 0.18-0.25 mm, 0.5-1.14 mm, 0.18-1.14 mm or intermediate, larger or smaller diameter. In some examples, when the tool is a microcatheter, the distance between the wheels is equal to or shorter than a microcatheter diameter, for example, between 2-3 FR. In some examples, when the tool is a guiding catheter, the distance between the wheels is equal to or shorter than a guiding catheter diameter, for example, between 309 FR.

In some embodiments, all wheels rotate at a similar rotational direction and speed. In some embodiments, the tool is firmly grasped between the opposing wheels, for example so that upon rotation of the assembly as a whole, the tool is caused to roll about its long axis.

In some embodiments, at a compressed state of the springs, wheels 409, 411 are retracted away from the tool, releasing hold of the tool. Optionally, a retracted position of the wheels facilitates insertion and/or removal of the tool from the channel. In some embodiments, compression of the springs is actuated via a knob or button, for example configured externally to the housing. In an example, rotation of the knob adjusts tension on the springs.

In some embodiments, the plurality of springs are actuated together as a single unit, so that all springs compress (or decompress) at once.

FIGS. 5A-C are different views of a driving assembly for moving a tool, according to some embodiments.

In some embodiments, an assembly of driving wheels 501 for moving a tool 503 (e.g. a guidewire) comprises multiple adjacent pairs of opposing wheels. In some embodiments, the wheel pairs are alternatively arranged on different planes which cross each other, for example so that a first series of wheel pairs lies on a first plane 507, and a second series of wheel pairs lies on a second plane 509, and the wheel pairs of both series intervene with each other.

In some embodiments, adjacent pairs of wheels include, for example, at least two wheel pairs closely positioned relative to each other, for example such that spaces defined between opposing wheels of each the two pairs are at an axial distance of no more than 20 mm, 10 mm, 5 mm, 1 mm, 0.5 mm or intermediate, longer or shorter distance.

In some embodiments, an angle between planes 507 and 509 is between 30-120 degrees, such as 60 degrees, 90 degrees, 11 degrees, or intermediate, larger or smaller angle. In a specific example, planes 507 and 509 are perpendicular (defining a "+" shaped arrangement).

In some embodiments, tool 503 extends along an elongate channel defined by the small spaces between opposing wheels of the multiple pairs.

Some potential advantages of an assembly of driving wheels which are alternately arranged on different planes that cross each other may include effectively utilizing a volume around the tool: such arrangement provides for fitting, optionally, a large number of driving wheels in yet a relatively small volume; having the wheel pairs engage the tool at multiple locations along the length of the tool, where optionally a distance between adjacent contact locations of the wheel pairs with the tool, as measured for example along the length of the tool, is less than 6 mm, 6 mm, 5 mm or intermediate, longer or shorter distance) optionally, the distance depends on the diameter of the driving wheels used); reducing spatial interference between wheels of adjacent pairs (as each pair lies on a different plane); potentially, segments of the tool that are located in between the adjacent wheel pairs allow access to the tool (for example, to load the tool and/or remove the tool and/or manually adjust a position of tool, optionally in an emergency situation or malfunctioning).

In some embodiments, as shown for example in FIG. 5C, each of the wheels of a series on at least one side of the channel is coupled to a frame 511 which includes a spring 513 configured to advance and/or retract the wheel that is coupled to the frame upon the spring being tensioned and/or released.

In some embodiments, an elongate rod 515 passes through the plurality of frames and interfaces with them. In some embodiments, rod 515 is operably attached to a gear 517 (for example, at one of the ends of the rod) which when rotated rolls the rod, thereby changing tension on (compressing or decompressing) the springs 513. In some embodiments, two elongate rods (of the two series, each arranged on a different plane) are rolled simultaneously, for example by rotation of a knob gear 519 which is coupled to the gears 517 of both rods, so that when knob gear 519 is rotated, gears 517 rotate as well, rolling rods 515 to change tension on the springs, which thereby retract the wheels from the channel or advance the wheels towards the channel. A potential advantage of an arrangement of rods and their actuating gears for example as shown in FIG. 5C may include simultaneously setting a position of the wheels of both series (relative to the channel) via a single component, for example by rotation of the knob gear.

In some embodiments, rotation of driving wheels 501 is actuated by a motor (not shown). Optionally, a plurality of transmission gears (not shown) transfer torque from the motor to the driving wheels.

In some embodiments, each series of wheels (i.e. wheel pairs lying on a single plane) includes for example between 2-16 wheels, for example arranged as 1-8 pairs. In such construction, the full assembly (including the two series) includes for example between 4-32 wheels in total, arranged for example as 2-16 pairs.

In some embodiments, the total number of wheels is selected so that sufficient traction is provided, for example by having a large enough number of contact locations between the tool and each of the wheels. Some potential advantages of multiple contact locations between the tool and each of the wheels may include: reducing a risk of slippage of the tool, improved grasping of the tool (such as in between the opposing wheels of each pair), and an ability of using of the wheels as pinching elements of the guidewire during rotation, allowing to reduce the individual pinching forces applied by each wheel pair onto the tool for gaining a same total grasping force of the tool with less impact on the tool surface.

It is noted that additional driving wheel arrangements are contemplated herewith. In some embodiments, wheel pairs may be arranged to lie on multiple planes, for example, on more than two planes. In an example, wheel pairs are helically arranged about the long axis in a spiral configuration.

In some embodiments, the channel defined by the plurality of spaces between opposing wheels of adjacent pairs is a linear, straight channel. Alternatively, the channel comprises one or more curvatures.

FIGS. 6A-B show a construct for linearly moving and/or rotating a tool, according to some embodiments.

FIGS. 6A-B are views from two different angles of a construct 601 configured to receive a tool (e.g. a guidewire), according to some embodiments. In some embodiments, the construct is housed within in an upper portion of a robotic device for example as described herein.

In some embodiments, the construct includes an assembly of driving wheels (hidden in these figures), for example as described in FIGS. 5A-C, which are positioned to contact a tool that is passed through the construct (such as passed in its designated channel, in-between the driving wheels and along the length of the construct). In some embodiments, the driving wheels assembly is substantially centered with respect to the whole construct.

In some embodiments, the construct comprises one or more motors, for example a motor 605 configured to actuate rotation of the driving wheels. In some embodiments, motor 605 is configured to rotate with the construct as a single unit when the construct is rotated. Optionally, motor 605 is axially aligned with the construct.

In some embodiments, another motor 604 is configured to actuate rotation of the construct as a whole, including rotation of motor 605 and motor 604 themselves. In some embodiments, motor 604 is positioned within a space formed in the construct. In some embodiments, motor 604 is configured to be positioned within this space, without extending beyond the perimeter defined by the construct's edges.

In some embodiments, a plurality of transmission gears 603 transfer torque from motor 604 to a large gear wheel 606 which when rotated rotates the construct as a whole.

In some embodiments, the construct comprises a plurality of transmission gears 607, which transfer torque from motor 605 to the driving wheels which linearly move the tool. Optionally, the transmission gears are located radially externally to the driving wheels. Optionally, rotation of each driving wheel is driven by one or more transmission gears. In some embodiments, a number and/or shape and/or position and/or size of the transmission gears is selected to modify the speed of rotation dictated by the motor. For example, the transmission gears reduce the speed of the motor. In some embodiments, all driving wheels are driven by the transmission gears at a similar speed. In some embodiments, at least 2, 4, 10, 14, 16, 20 or intermediate, larger or smaller number of transmission gears are positioned and configured to drive movement of each of the pairs of driving wheels.

In some embodiments, the construct is coupled to slip ring 609 through which electrical power may be supplied to the one or more motors. In some embodiments, slip ring 609 is configured to ensure electrical contact at all rotational orientations of the construct. In some embodiments, slip ring 609 is axially aligned with the construct.

In some embodiments, in use, linear movement (advancement and retraction) of a tool received within the construct is carried out in the following manner: motor 605 drives rotation of transmission gears 607, which in turn optionally adjust the speed of rotation and transfer torque from the motor to the driving wheels (not shown), which are in held in close contact with the tool. In some embodiments, roll movement of the tool is carried out by rotation of gear 606 operated by motor 604 via transmission 603, where gear 606 rotates the construct as a whole, causing the tool held by the driving wheels to roll about its long axis.

As can be further observed, in some embodiments, a knob 611 which is optionally external to the device housing drives simultaneous rotation of gears 613, each of which is coupled to an elongate rod (not shown). When each of the rods is rotated, it changes the tension applied onto a plurality of springs (not shown) to either approximate or pull away each of the driving wheels that are coupled to the springs from their opposing driving wheels.

In some embodiments, construct 601 is compactly arranged so that its components are maintained within a limited radial extent, for example, a radius at a cross section of a substantially cylindrical construct is less than 3.5 cm. Optionally, a volume of the construct is smaller than 500 cm^3.

In some embodiments, components forming the construct are co-centrically arranged about a similar long axis. In some embodiments, gear 606 and/or slip ring 609 are arranged to lie on planes that are substantially perpendicular to a long axis of the construct, and do not protrude more than 5%, more than 10%, more than 15% or intermediate, larger or smaller percentage beyond a perimeter defined by the construct. A potential advantage of a compact co-centrical arrangement of the components of the construct may include maintaining a relatively short radius of rotation of the construct, when rotated as a single unit (such as to generate roll of the tool).

FIGS. 7A-C show an assembly for linearly moving a tool, according to some embodiments.

In some embodiments, assembly 701 is configured for linearly advancing and/or retracting a tool 703, such as a guidewire, microcatheter or guiding catheter.

In some embodiments, the assembly comprises a plurality of driving wheels 705, optionally arranged in two parallel rows, such that each pair of opposing wheels defines a path therebetween for receiving the tool.

In some embodiments, wheels of at least one of the rows of the assembly are coupled to elastic elements such as springs 707 which move the wheels towards or away from tool 703 upon change in tension. In some embodiments, each driving wheel is coupled to a spring. Alternatively, a plurality of driving wheels of a row, and optionally, all driving wheels of a row are coupled to a same spring (such as via a connecting frame or rod, not shown). In some embodiments, spring 707 is encased within a compartment 709. In some embodiments, tension on the springs is modified via rotation of knob 711 which in turn rotates a rod 713 that extends axially across all compartments 709, and pulls or compresses the springs once rotated.

In some embodiments, a plurality of transmission gears 715 are positioned in operable contact with the driving wheels 705 and are configured to transfer torque from a motor (not shown) and/or to adjust the actuation speed dictated by the motor.

In some embodiments, at an entry and/or exit location of the channel in which the tool passes, a seal 717 is provided. In some embodiments, the seal includes an aperture which can be pushed open by advancement of the tool through. In some embodiments, the seal hermetically surrounds the tool around the aperture, preventing fluid (e.g. saline, blood, water) from flowing into the channel between the driving wheels.

Integral Connector

FIG. 8 is a schematic diagram of a connector which is integral with the device housing, according to some embodiments.

In some embodiments, a compact robotic device for example as described herein includes one or more integrated connectors, such as Y-connectors which are provided inside the housing of the device. In some embodiments, the connector is pre-mounted (such as during manufacturing of the device) at a selected spatial position inside the device, for example where the connector is aligned with a channel in which a tool is received.

In some embodiments, connector 801 includes a stem portion 803 and one or more branches 804 extending at an angle from the stem portion. In some embodiments, the stem serves as an access portal for insertion of the tool and for linear movement of the tool. In some embodiments, angle 802, which is defined between the branch and the stem portion that is closer to an entry point into the patient body (distal portion), is smaller than 90 degrees. In some embodiments, the branch extends at angle 802 of, for example, 30 degrees, 50 degrees, 60 degrees, 20 degrees or intermediate, larger or smaller angle relative to the distal stem portion. Therefore, in a complementary fashion, an angle (not numbered) formed between the branch and the proximal stem portion is larger than 90 degrees, for example 95 degrees, 110 degrees, 130 degrees, 160 degrees or intermediate, larger or smaller angle.

In some embodiments, the proximal stem portion comprises a seal allowing the tool to pass through yet preventing the passing of fluid from entering the driving assembly of the tool. In some embodiments, an angle smaller than 90 degrees is defined between the branch and a stem portion which does not contain the seal; while a complementary angle which is larger than 90 degrees (adding up to 180 degrees with the small angle) is defined between the branch and a stem portion in which the seal is located.

In some embodiments, the connector is at least partially located inside the device housing (schematically indicated by 805). In some embodiments, stem 803 is linearly aligned with the channel 807 for the tool. By an aligned connection of the stem and the channel, a risk of navigating a tool into branch 804 instead of into the stem 803 and/or channel 807 is potentially reduced. Potentially, due to the small angle of the branch relative to the stem portion through which the tool is inserted, a risk of navigating the tool into the branch instead of into the continuing portion of the stem (and further into the channel) is reduced.

In some embodiments, branch 804 extends, at least partially, externally to housing 805. Optionally, in use, fluids (e.g. saline, water, medication) are injected through branch 804 to be introduced into the lumen of a tool (e.g. a microcatheter lumen, a guiding catheter lumen) to be entered into the patient's body. In some embodiments, entry of the injected fluid into channel 805 is prevented by a seal 809 positioned along the stem 803 beyond the juncture of branch 804 with stem 803. Optionally, the seal is structured to allow a tool to pass through, and hermetically surrounds the tool to prevent fluid from entering the channel. In some embodiments, the injected fluid flows into the connector through branch 804 and when it reaches the seal 809 the fluid is caused to "turn around" to then flow in an opposite direction from the stem, and optionally into a lumen of a tool.

In some embodiments, housing 805 of the device is transparent at least at wall portions located adjacent and around the connector, for example to provide for visual detection of blockage and/or presence of clots at the connector.

In some embodiments, connector 801 comprises one or more sensors 811, such as optic sensors and/or pressure sensors and/or other sensors configured to detect one or more of: presence of a tool in the connector, presence of injected fluid in the connector, movement of a tool in the connector, FIGS. 9A-B are internal views of a robotic device comprising an integral connector, according to some embodiments.

In the example shown, a connector which constitutes a fixed, optionally inseparable component of the device comprises a stem 903 which is axially aligned with a channel in which a tool such as a guidewire 905 is passed, and a branch 907 extending from the stem.

In some embodiments, the connector is positioned adjacent the tool driving assembly 915 (in this example, proximally to the driving assembly). A potential advantage of a connector positioned directly adjacent the tool driving assembly may include effectively reducing a length of the tool which is "used up" by manipulating and connecting elements, leaving a longer segment of the tool available for use (such as for insertion to the body). For example, if a connector was placed at a distance from the driving assembly, the tool segment extending in between the driving assembly and the connector would effectively be wasted, as compared to the shown arrangement, in which the tool passes through the connector immediately after passing through the driving assembly (or vice versa).

In some embodiments, a branch 907 of the connector extends from the stem and at least partially externally to walls of a housing 911 of the device, having an aperture 912 located outside the housing.

In some embodiments, proximally to the stem and outside the walls of the housing, a luer 913 (or any other suitable connector) is mounted and configured for receiving a proximal end of tool such as a microcatheter for attachment of the microcatheter to the device.

In an exemplary method of loading the device, guidewire 905 is introduced in a proximal direction (see arrow 916) which is opposite to the direction of introducing the guidewire into the patient body, into lumen of the stem 903, optionally through luer 913, and advanced into its channel defined between the wheels of the driving assembly 915 with the tool's proximal end being the leading end. Once a microcatheter proximal end (not shown) is attached at luer 913, the guidewire can be advanced in a distal direction to enter the lumen of the microcatheter.

In use, in some embodiments, fluid 917 that is injected through branch 907 reaches a seal 919 of the connector, and is then forced to turn and flow distally through stem 903 to enter a lumen of the microcatheter. In some cases, due to that the device as a whole is, in some embodiments, disposable, it may be allowed for a small amount of fluid to enter the vicinity of the driving assembly and even contact the wheels, as long as the fluid remains at a level which does not substantially interfere with manipulation of the tool by the driving assembly.

Rail Mechanism

FIGS. 10A-C show a rail mechanism for sliding movement of the robotic device together with its assembled tools, according to some embodiments.

In some embodiments, device 1001 comprises or is attached to a rail mechanism which provides for the device to slide, as a whole and including the tools loaded onto the device, linearly with respect to an elongate rail 1005. In some embodiments, a length 1007 of the rail is between 2-7 cm long, and the robotic device is configured to slide back and forth on the rail along its length.

In some embodiments, a housing 1009 of device 1001 comprises one or more protrusions 1011 which fit into one or more designated recesses in a support fixture 1013. In some embodiments, the support fixture comprises the rail. Alternatively, the rail is included as part of the device housing and during sliding of the device relative to the rail, the protrusions slide in their recesses. In an example, the protrusions are received within a slot shaped recess. In some embodiments, sliding movement of the device on the rail is actuated by a gear 1012, where rotation of the gear may be driven by a motor inside the device, and/or an external motor.

In some embodiments, sliding movement of device 1001 with respect to the support fixture which holds the device with respect to the patient, provides for fine-tuning a location of the one or more tools that are loaded onto the device relative to the patient's body, for example relative to an entry point to the body.

In some embodiments, one or more sensors are positioned and configured to detect a relative axial position of the device on the rail, for example to provide an indication of the extent the device can be further advanced or retracted on the rail. For example, one or more optic sensors are positioned on rail 1005 and/or on support fixture 1013. In some embodiments, the attachment between the device housing and the support fixture aligns the device relative to the rail, for example so that the device homing position is at the center of the rail, allowing for movement in both directions along the rail.

Methods for Detecting and Positioning a Tool

FIG. 11A is a flowchart of a method for setting a reference position of an elongate tool in its designated channel of the robotic device, according to some embodiments.

In some embodiments, the robotic device comprises one or more sensors, for example sensors configured to detect presence and/or a relative position of a tool loaded onto the device. In some embodiments, the one or more sensors are positioned along the channel in which the tool is received. Optionally, a plurality of sensors (e.g. optic sensors) are positioned at a plurality of axial positions along the channel and/or at a plurality of circumferential positions of the channel. In some embodiments, for example in the case of a channel that is large in volume, different sensors may be provided for covering different portions of the total volume of the channel.

In some embodiments, sensing of presence of a tool is performed for calibration purposes, for example to set a reference axial position for the tool relative to the long axis of the channel.

In some embodiments, at 1101, an elongate tool is introduced into its channel and advanced (manually and/or automatically) into a first axial position in the channel, in which presence of the tool (or a selected portion of it, such as a distal end or a proximal end of the tool) is detected by one or more sensors of the channel.

Then, at 1103, the tool is advanced or retracted to a second position in which the tool is no longer detected by the sensor(s). In some embodiments, the number of motor rotations required to move the tool from the first position to the second is counted, e.g. by an encoder of the motor.

At 1105, the second position is set as a reference location for the tool, so that at 1107, linear movement of the tool within the channel can be controlled using the second position as reference, based on the measured actuation required for moving the tool from the first position to the second position, e.g. based on the counted number of motor rotations.

In some embodiments, during manipulation of the tool, using the counted number of motor rotations required for moving the tool from the first position to the second, quick retraction or advancement of the tool from or to the reference location may be carried out by automated activation of the motor to rotate the counted number of rotations. A potential advantage of automated retraction and/or advancement of the tool which is carried out, for example, by commanding the motor to rotate the counted number of rotations, may include faster movement of the tool for example as compared to manually controlled advancement or retraction.

In some embodiments, automatic advancement of the tool is performed from the second position to a third position, the third position being located proximally to the first position and distally to the second position. Optionally, in order to bring the distal end of the tool to the third position, the tool is advanced automatically by commanding the motor to rotate less than the counted number of rotations, for example, by reducing a predetermined number from the count of rotations that were required to move the tool between the first and the second positions. The distance between the first position and the third position can be, for example, 1, 2, 3, 4, 6, 8, or 10 cm, or intermediate, longer or shorter distance. A potential advantage of returning the tool to a third position being proximal relative to the original first position lies in safety considerations. For example, the tool is automatically advanced back into the patient at a relatively high speed up to the third position, but the physician controls the speed and amount of advancement beyond the third position, which is closer to the point of interest and may include a more sensitive environment.

In some embodiments, automatic advancement of a tool is to a predetermined axial distance, optionally set regardless of the tool initial and/or current position. For example, following automated retraction of a tool, a command signal to advance the tool will cause the tool to be moved distally a set predetermined distance. Optionally, the set predetermined distance is determined according to the one or more other tools being telescopically used with the moved tool, for example according to their length. In an example, a guidewire is set to be advanced a predetermined distance of, for example, 1 meter, for example being the shortest microcatheter length available. A potential advantage of setting a predetermined distance for advancing the tool may include reducing or preventing a situation in which a tool is advanced beyond (or does not surpass a preset distance beyond) a distal end of a second tool throughout which the first tool extends.

In some embodiments, tool advancement and retraction are performed at a position of a connector. In an example, a guidewire is retracted to allow injection of fluid (e.g. contrast agent) into the lumen of a microcatheter, and following injection, the guidewire is advanced once again into the microcatheter lumen. In such exemplary configuration, automated retraction and advancement of the tool may accelerate and facilitate the injection process.

FIG. 11B schematically shows a tool 1109 in the first position, being detected by one or more sensors 1111 of a channel 1113; FIG. 11C schematically shows the tool 1109 in the second position, where it is no longer detected by the one or more sensors 1111.

Exemplary Method of Loading a Compact Robotic Device with Elongate Surgical Tools FIG. 12 is a flowchart of a method for loading elongate surgical tool(s) onto the compact robotic device, according to some embodiments.

In some embodiments, prior to performing a surgical procedure, the compact robotic device is loaded with one or more elongate surgical tools, which are then manipulated by the device.

The following method is an example for loading the device. It is noted that the steps may be carried out manually (e.g. by a physician, surgeon, nurse or other clinical personnel) or, in some embodiments, automatically.

In some embodiments, a guidewire portion is introduced into a designated channel of the device (1203), for example, a proximal portion of the guidewire. In some embodiments, a more distal portion of the guidewire, optionally including the guidewire distal end, is introduced into a lumen of a microcatheter (1203). The microcatheter proximal end is then coupled to the device (1205), for example at a luer disposed on the device housing, or via another suitable connector. Then, a microcatheter portion is introduced into a designated channel of the device (1207). In some embodiments, the microcatheter forms a curve outside the device housing, for example between a connection of the microcatheter proximal end to the luer and the entry aperture of a more distal portion of the microcatheter into the designated channel.

In some embodiments, when a guiding catheter is used, the microcatheter (including the guidewire threaded therein) is advanced into a lumen of the guiding catheter (1209). The guiding catheter proximal end is then attached to the device (1211) for example at a luer disposed on the device housing, or via another suitable connector.

In some embodiments, loading of the device involves introducing the guidewire first into contact with the device assemblies, and then introducing the additional tools (e.g. microcatheter and optionally then a guiding catheter) using the guidewire as a backbone for the telescopic arrangement of all tools. In some embodiments, the guidewire serves as an introducer which is introduced together with the additional tools into their designated channel inside the robotic system. In some embodiments, as detailed in the example of FIG. 12, the guidewire is introduced into its designated channel first and is then used to guide additional tools into their channels. Alternatively, the guidewire is first used to introduce the additional tools using its distal end, and only then it is threaded through its proximal end into its own designated space.

In some embodiments, a user controls manipulation of the tools loaded onto the device (1213), for example by controlling linear movement and/or rotation of the tools driven by the device assemblies. In some embodiments, control is performed remotely, for example via a remote control, console or the like.

It is noted that a loading method as described is provided only as an example, and that the described steps may be carried out in a different order, and/or that different steps will be performed. In some embodiments, some of the steps are carried out manually and/or are aided by a user, while some of the steps (e.g. advancing, retracting and/or rolling a tool) into a desired position and/or orientation are carried out automatically by the device.

Exemplary Guiding Catheter Assembly

FIG. 13 is an example of an assembly for coupling a guiding catheter to the compact robotic device and for moving the guiding catheter using the compact robotic device, according to some embodiments.

In some embodiments, a guiding catheter is coupled to the robotic device externally to the device housing, yet assemblies for manipulating the guiding catheter are positioned, at least in part, inside the device housing. In some embodiments, the guiding catheter assembly is configured as an add-on to the robotic device. Alternatively, the guiding catheter assembly is integral with the device.

In some embodiments, a proximal end of a guiding catheter 1301 is connected to the device housing, for example via a luer 1303.

In some embodiments, the luer is coupled to one or more gears 1305 which when actuated by a motor 1307 generate rotation of the luer, rolling the guiding catheter.

In some embodiments, only the luer 1303 extends externally to the housing, while the other components (e.g. motors, gears) for driving movement of the guiding catheter are accommodated inside the volume of the device housing, optionally in proximity to the driving assembly of a microcatheter.

In some embodiments, linear movement (e.g. advancement and/or retraction) of the guiding catheter is carried out by moving the device, as a whole, for example by sliding movement of the device relative to a rail (for example as shown in FIGS. 10A-C). In some embodiments, a sliding movement of the device on the rail is generated by a motor 1309.

In some embodiments, a connector 1311 is positioned in communication with luer 1303, for example allowing for injection of fluid into a lumen of the guiding catheter, via the luer. In some embodiments, the connector is integrated in the device housing (not shown), and only a branch portion of the connector extends outwardly from the housing.

In some embodiments, one or more sensors such as an optic sensor 1313 are positioned and configured to identify when a tool such as a guidewire and/or a microcatheter has been retracted from a lumen of the guiding catheter, freeing the guiding catheter lumen for introducing (e.g. by injection) other materials (e.g. contrast agent).

FIG. 14 is a schematic block diagram of a robotic device configured for manipulating two or more elongate surgical tools, according to some embodiments.

In some embodiments, walls of a housing 2701 of the robotic device define an inner volume 2703 in which at least two distinct pathways (channels) such as 2705, 2707 for the elongate surgical tools are defined. In some embodiments, the pathways extend across the inner volume, for example, between two opposing walls of the housing, such as wall 2709 and wall 2711. Optionally, the housing is shaped in an elongated form, for example having a substantially rectangular cross section profile, and the pathways extend along the length of the housing.

In some embodiments, each of the pathways extends between an entry aperture formed at the wall of the housing, and an exit aperture formed at an opposite wall of the housing. In the example shown, pathway 2705 extends between entry aperture 2713 formed at wall 2709 and an exit aperture 2715 formed at wall 2711; and pathway 2707 extends between an entry aperture 2717 formed at wall 2711 and an exit aperture 2719 formed at wall 2709.

In some embodiments, an aperture formed in a wall of the housing is shaped and/or sized according to the surgical tool that is passed through it. For example, a rounded (e.g. circular) aperture is sized for fitting a cylindrical tool, such as a guidewire or microcatheter, where the aperture diameter is optionally no more than 5%, 10%, 25% or intermediate, higher or smaller percentage larger than a diameter of the tool. In some embodiments, an aperture is sized for more than one tool to be passed through. Optionally, the aperture profile is oval (e.g. ellipsoid), rectangular, slot shaped and/or other. In some embodiments, a single elongated slot serves as an aperture for both inner pathways.

In some embodiments, a single tool passes through an entry aperture into the inner volume of the housing, and exits the housing through a respective exit aperture. Alternatively or additionally, in some embodiments, a plurality of tools telescopically arranged (e.g. 2 tools, such as a guidewire provided within the inner lumen of a microcatheter) pass together through the same entry aperture and exit the housing together through a respective exit aperture. Thus, in such an example, a first tool passes through a first inner pathway, exits the housing into the lumen of a second tool, and the telescopic assembly of both tools passes through a second inner pathway. In some embodiments, the telescopic arrangement of the tools occurs outside of the housing, after both tools have passed through their inner pathways, for example, in the case of a rapid exchange catheter which can be interfaced with the guidewire after each of the guidewire and the rapid exchange catheter have passed independently through their respective actuation assemblies located in the inner pathways.

In some embodiments, the pathways extend in a similar plane, for example, a similar horizontal plane, a similar vertical plane, a similar plane extending diagonally between the walls of the housing. In some embodiments, the pathways extend along parallel axes. A distance 2721 between the parallel axes may range, for example, between 3-12 cm, 2-10 cm, 5-9 cm or intermediate, longer or shorter distance.

Alternatively, in some embodiments, the pathways are not parallel, for example, one pathway extends directly between opposite walls while another takes a diagonal or other indirect route.

In some embodiments, except for the aperture locations, the housing is sealed. Optionally, the housing includes a removable or moveable cover or lid. In some embodiments, the housing is open at least in part, for example, shaped as a box with no top face.

In some embodiments, all components which engage the tool to manipulate it and/or to drive its movement are fully encased inside the inner volume of the housing and at least some of these components are positioned along the pathway defined for the tool. In some embodiments, these components include an actuation assembly, for example the tool-moving elements (e.g. driving wheels).

In some embodiments, as shown, a plurality of motors 2722, 2723 is configured to drive the actuation assemblies, for example configured to drive tool-moving elements 2725 (e.g. wheels) of each assembly. In some embodiments, the motor and the tool moving elements are positioned along the pathway defined for the tool. In some embodiments, the actuation assemblies of the two (or more) pathways are aligned side-by-side. A potential advantage of the actuation assemblies being aligned side-by side may include allowing for a short or minimal distance 2728 (optionally being the device width or height) between opposing walls 2733, 2735. In an example, distance 2728 is smaller than 15 cm, 12 cm, 10 cm or intermediate, longer or shorter distance.

In some embodiments, the actuation assemblies of the two or more pathways have a similar axial extent (or do not extend beyond a certain axial extent). A potential advantage of the actuation assemblies being positioned relative to each other and/or sized such that they do not extend beyond a certain axial extent may include that a distance 2730 between walls 2709 and 2711 (optionally being the device length) may be kept to a minimal axial extent needed to contain the movement driving components. In an example, distance 2730 is smaller than 10 cm, 7 cm, 12 cm or intermediate, longer or shorter distance. In some embodiments, the plurality of motors 2722, 2723 are also positioned within the axial extent of the actuation assemblies, and in proximity to the actuation assemblies, to facilitate the compact design of the device. The ability to position the motor(s) in close proximity to the actuation assemblies and potentially in contact with at least a portion of the actuation assemblies is provided, for example, due to that no barriers (e.g. sterile protection or shield) are needed between the actuation assembly, the motor(s), and the surgical tool being manipulated.

In some embodiments, the actuation assemblies of the two or more pathways are positioned within the same, shared inner volume defined by the walls of the housing. In some embodiments, no barriers (e.g. inner walls, shields, drapes, and the like) exist between the movement driving components of the two or more pathways. In some embodiments, no barriers (e.g. inner walls, shields, drapes, and the like) exist between the actuation assemblies and the tools that are being manipulated by them.

Alternatively, in some embodiments, a partial partition or barrier are provided. For example, the device housing may include an inner wall or protrusion which do not fully block the inner volume, leaving at least some regions of the pathways in communication with each other.

In some embodiments, an actuation assembly of an inner pathway (e.g. an actuation assembly that includes a shaft in which a tool is received and/or wheels which drive linear movement of the tool) is exposed to an actuation assembly of a different inner pathway, for example an adjacent pathway.

In some embodiments, actuation assemblies of a plurality of pathways are arranged and held with respect to each other on a chassis. Optionally, the chassis is exposed and open to its surroundings, for example, no housing is provided.

In some embodiments, an actuation assembly of a pathway at least partially restrict movement of the tool within the inner pathway, for example, restricting lateral movement of a tool received within the pathway. For example, movement of the tool out of notional limits defined by the elongate pathway is restricted. In some embodiments, the tool is channeled through the pathway, for example, received within a slot of an elongate shaft. Alternatively or additionally, the pathway is defined by a path generated between a plurality of pairs of opposing wheels.

In some embodiments, in addition to extending through the pathway, a tool engages the device at one or more additional fixation locations (also referred to herein as "securing points", "engagement points"). In some embodiments, a fixation location comprises a holder (such as 2727, 2729) located outside the housing, inside the housing, or partially inside the housing and partially outside the housing. In some embodiments, a fixation location couples a tool to the housing and/or to one or more other tools. For example, at fixation location 2729 a first elongate surgical tool 2731 which extends through pathway 2705 (e.g. a guidewire) enters an inner lumen of a second elongate surgical tool 2733 (e.g. a microcatheter), which is coupled to the housing at fixation location 2729. In some embodiments, a proximal end of tool 2731 is coupled to the housing at fixation location 2727.

In some embodiments, fixation location 2727 is shaped and configured to accommodate a proximal handle of tool 2731, for example, a handle that manipulates the distal portion of the tool in terms of bend and/or stiffness. In some embodiments, an additional motor (not shown) is configured for rotating tool 2731 through two locations, one of which is the handle of the tool (for example at fixation location 2727) and the other is a region more distal of the tool. For example, a motor configured for rotating tool 2731 by rotating an actuation assembly which is associated with a portion of the tool 2731, is also operably connected to the handle of the tool, optionally through a gear system. As such, the motor is configured for rotating the tool simultaneously from these two distinct locations. An advantage for commencing roll movement by the same motor in two different locations along the tool may include enhancing the torque applied on the tool and eliminating the risk of slippage of the tool in its gripping locations found in the actuation assembly.

In some embodiments, a fixation location of a tool with the housing (such as 2727) and an entry aperture leading the tool into the inner volume (such as 2713) are located on a same wall of the housing, so that a section of the tool that is found outside the housing forms a curve, for example, a U-shaped curve. In some embodiments, the extent of the U-curve is dynamically adjustable. Optionally, linearly moving the tool (such as via the tool-moving elements, e.g. wheels) changes the extent of the U-curve relative to the external side of the wall of the housing.

In some embodiments, the curve is defined along a path which extends from and to the same wall of the device housing.

In the example shown, the housing comprises sharp corners and straight edge walls, but other configurations are also contemplated, including, for example, rounded corners, curved walls, and the like.

In some embodiments, actuation of the actuation assembly (e.g. via a motor) of each of the pathways is controlled by a controller 2735. In some embodiments, components of each pathway are controlled independently, yet in a synchronized manner.

In some embodiments, controller 2735 is controlled remotely by an external device, for example by a remote control device such as described herein.

FIG. 15 schematically illustrates a robotic device for manipulation of two or more elongate surgical tools configured for a telescopic arrangement, such as in a non-limiting manner a guidewire and a microcatheter, the first elongate tool extending at least in part within the lumen of the second elongate tool, according to some embodiments.

In some embodiments, robotic device 2801 comprises a housing 2803 comprised of a plurality of walls which form an inner volume 2805 between them. In some embodiments, two or more inner pathways extend inside the inner volume, such that tools 2810, 2813 received and operated by the device extend, at least in part, along the inner pathways.

In some embodiments, each of the inner pathways includes an actuation assembly positioned at a position of the pathway, for example, axially extending along at least a portion of the pathway. In some embodiments, an actuation assembly, such as 2806, 2807, is configured for linearly moving the tool, for example, one or more sets of wheels configured to advance and/or retract the tool. Alternatively or additionally, an actuation assembly, such as 2806, is configured for moving the tool in a roll manner, for example by rotating a set of wheels gripping the tool therebetween.

In some embodiments, actuation assemblies are operably coupled to a plurality of motors, for example motors 2811, 2808, 2809. In some embodiments, the motors are configured for operating the actuation assemblies to generate linear movement of the tools received therein. Alternatively or additionally, the motors are configured to generate a roll movement of the received tool, optionally by generating a roll movement of the tool's associated actuation assembly as a whole. For example, motor 2809 is operably connected to linear movement mechanism 2807, optionally via a gear system, and is configured to rotate linear movement mechanism 2807 together with motor 2811, thereby rolling tool 2810 which is gripped within linear movement mechanism 2807. A potential advantage for rotating the entire linear movement mechanism along with the tool is a simplification of the associated gear system, and the enablement of simultaneous operation of linear and roll movement together. Rolling of motor 2811 together with the linear movement mechanism 2806 is enabled, in some embodiments, due to that no sterile barrier exists between the motors and the actuation assemblies.

In the example shown, a first elongate surgical tool 2810 (e.g. a guidewire) extends along a first inner pathway, for example between an entry aperture 2814 into the housing and an exit aperture 2816 from the housing.

In some embodiments, linear movement of tool 2810 is driven by motor 2811, and roll of tool 2810 is driven by motor 2809, both located and configured at a position of the inner pathway (e.g. along a notional axis defined by the pathway across the inner volume).

In some embodiments, at the exit aperture 2816 of tool 2810 from the housing, the tool 2810 is telescopically received within a lumen of a second elongate surgical tool 2813, for example, a microcatheter. Tool 2813, in turn, enters the housing at an entry aperture 2815 and extends along a second inner pathway to an exit aperture 2817, with tool 2810 extending inside it.

In some embodiments, linear movement of the tool 2813 is driven by actuation assembly 2807.

In some embodiments, the actuation mechanism(s) and the plurality of motors all share the same inner volume, with no barrier or other physical separation therebetween.

FIG. 16 schematically illustrates another exemplary embodiment of the robotic device configured for receiving three telescopically arranged elongate surgical tools, for example, a guidewire, a microcatheter and a guiding catheter.

In some embodiments, robotic device 2901 comprises a housing 2903 having an inner volume 2905, wherein entry aperture 2914 and exit aperture 2916 define, between them, a first inner pathway for receiving a first elongated surgical tool 2910, and entry aperture 2915 and exit aperture 2917 define, between them, a second inner pathway for receiving a second elongate surgical tool 2913.

In some embodiments, actuation assemblies 2906, 2907 are positioned along the inner pathways and configured to come into contact with the tools received therein for at least one of advance, retract and/or roll the tool. In some embodiments, a plurality of motors, such as motors 2909, 2911 and 2908, are positioned in proximity to the inner pathways and are operably connected to the actuation assemblies. In some embodiments, the motors and the actuation assemblies are found within the same inner volume accommodating the inner pathways, for example without barriers blocking the air circulating between them.

In some embodiments, only one motor is operably connected to an actuation assembly, as exemplified by actuation assembly 2907 and motor 2908, which is operably connected to the actuation assembly to advance or retract elongate surgical tool 2913. In some embodiments, two or more motors are operably connected to an actuation assembly, as exemplified by actuation assembly 2906 and motors 2909 and 2911. In this example, motors 2909 and 2911 are operably connected to actuation assembly 2906 to advance, retract and roll elongate surgical tool 2910. Optionally, motor 2909 rolls tool 2910 by rolling the complex 2904, wherein complex 2904 comprises at least actuation assembly 2906 and motor 2911.

In some embodiments, the proximal end of elongate surgical tool 2910 is secured to a fixation location 2920. In some embodiments, fixation location 2920 includes a protrusion configured to attach to a luer (not shown) optionally found in the proximal end of tool 2910. Alternatively, fixation location 2920 comprises a cavity sized and shaped to accommodate a handle (not shown) optionally found at the proximal end of tool 2910. In some embodiments, the proximal end of tool 2910 is operably connected to adaptor 2950 which, in some embodiments, causes the tool to roll around its longitudinal axis, for example by roll of a proximal handle portion of the tool which is received at the adaptor. In some embodiments, the motor which is operably connected to the adaptor to induce the roll movement, is the same motor operably connected to the actuation assembly associated with the tool at a more distal location. For example, as shown and exemplified through motor 2909, which is operably connected to adaptor 2905 and at the same time operably connected to complex 2904, to cause roll actuation of tool 2910 from at least these two distinct locations.

In some embodiments, a U-shape curve is formed in tool 2910 between fixation location 2920 and entry aperture 2914. In some embodiments, when tool 2910 is moved linearly in actuation assembly 2906 it causes the distal end 2930 of tool 2910 to advance or retract, optionally when a distal portion has been introduced into the patient's body. In some embodiments, as tool 2910 is advanced or retracted, a distance between a maximal point of the U-shape curve and housing 2903 is shortened or lengthened. An advantage of the U-shape curve being formed outside of housing 2903 is that the housing size does not need to accommodate this distance, and the device is capable of navigating a range of tool lengths, with no dependency on the size of the device.

In some embodiments, a fixation location of one elongate surgical tool is found at the exit aperture of another elongate surgical tool, as shown and exemplified in fixation point 2922, which overlaps with exit aperture 2916, and as such, causes elongate surgical tool 2910 to exit housing 2903 through exit aperture 2916 directly into the lumen of elongate surgical tool 2913, when tool 2913 is connected to fixation location 2922.

In some embodiments, a second U-shaped curve for tool 2910 and a first U-shaped curve for tool 2913 are formed between fixation location 2922 and entry aperture 2915. In some embodiments, when advancing or retracting the distal end 2940 of tool 2913, both tool 2910 and tool 2913 are moved to lengthen or shorten the distance between the maximal point of the joint curve and housing 2903. In some embodiments, when it is desired to linearly translate the distal end 2940 (of tool 2913) without translating distal end 2930 (of tool 2910), motor 2911 linearly translates tool 2910 at an opposite direction to the translation of motor 2907 which affects both tools, thereby, causing the distal end 2930 of tool 2910 to effectively to stand in place.

In some embodiments, an elongate surgical tool (for example, a guide catheter, or sheath) connected to a fixation location from outside of housing 2903 is configured to be operated by motors residing inside housing 2903, for example, elongate surgical tool 2919 connected to fixation location 2917 and can be linearly moved actuation assembly 2927, operably connected to motor 2928 and motor 2929 for linear and roll movement, respectively. In some embodiments, actuation assembly 2927 together with motors 2928 and 2929 all reside in the same inner volume as motors 2909, 2911 and 2908 and in the same inner volume as the actuation assemblies they are operably connected to, 2906 and 2907. In such exemplary embodiments, at least 5 motors reside within the same inner volume as the inner pathways of the elongate surgical tools 2910 and 2913.

In some embodiments, fixation location 2924 overlaps with exit aperture 2917, such that the telescopically arranged elongate surgical tools 2910 and 2913 exit housing 2903 through exit aperture 2917, directly into the lumen of elongate surgical tool 2919. In some embodiments, actuation assembly 2927 is positioned along the same inner pathway as that of tool 2913.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for controlling linear movement of an elongate surgical tool at least partially received in a designated channel of a compact robotic device, comprising:

positioning said elongate surgical tool at a first position within said designated channel inside the robotic device, wherein presence of said elongate surgical tool in said first position is detectable by one or more sensors located at said channel;

positioning said elongate surgical tool at a second position within said channel, wherein at said second position said presence of said elongate surgical tool is not detectable by said one or more sensors; and upon receipt of a command to move said tool linearly along said channel, using said second position for calibrating movement of said tool.

2. The method according to claim 1, wherein said positioning comprises advancing or retracting said tool along said channel.

3. The method according to claim 1, wherein a portion of said tool which is being detected by said one or more sensors comprises one of: a distal end segment of said tool, a proximal end segment of said tool.

4. The method according to claim 1, wherein said one or more sensors include optic sensors.

5. The method according to claim 1, comprising counting, via an encoder, a number of motor rotations required for moving said elongate surgical tool from said first position to said second position, and then using said counted number for automated retraction or advancement of said elongate surgical tool between said first and second positions.

6. The method according to claim 5, wherein said automated retraction or advancement is to a third position located a predetermined distance from said first position.

7. The method according to claim 5, wherein said automated retraction or advancement is to said third position located a predetermined distance from said second position.

8. The method according to claim 1, wherein said compact robotic device comprises:

a housing including walls which define an inner volume containing:

at least one elongate channel for receiving said elongate surgical tool, the channel having at least one first aperture leading into or out from said housing;

a driving assembly for driving one or both of linear movement and roll movement of the elongate surgical tool, when said surgical tool is received within said channel;

at least one connector in communication with said channel, said connector comprising a branch defining a second aperture located at or externally beyond said walls of said housing, said second aperture being separate from said first aperture of said channel.

9. The method according to claim 8, wherein said connector comprises a stem portion which is aligned with said channel, and said branch extends at an angle from said stem portion.

10. The method according to claim 9, wherein said branch extends at an angle of less than 90 degrees relative to a long axis of said stem portion which is aligned with a direction of advancement of said elongate surgical tool into a patient body.

11. The method according to claim 8, wherein said connector is formed as an integral component of said compact robotic device.

12. The method according to claim 8, wherein said walls of said housing at a location of said connector are formed of a transparent material or comprise a window allowing visual access of said connector.

13. The method according to claim 9, comprising a seal located at a proximal portion of said stem portion, said seal shaped and configured to allow an elongate surgical tool to pass through and hermetically surround said elongate surgical tool thereby preventing fluid injected through said branch from entering said channel.

14. The method according to claim 13, wherein said branch extends at an angle of more than 90 degrees relative to a long axis of said stem portion containing said seal.

15. The method according to claim 8, wherein said at least one connector comprises one or more sensors configured to detect one or more of: a presence of the tool in the connector, a presence of injected fluid in the connector and a movement of a tool in the connector.

* * * * *